United States Patent
Tello Reyes et al.

(10) Patent No.: US 12,246,045 B2
(45) Date of Patent: Mar. 11, 2025

(54) **METHOD FOR PREPARING A TRANSFORMED, *SALMO SALAR* INTERFERON GAMMA (IFNG)-PRODUCING *LACTOCOCCUS LACTIS* BACTERIUM**

(71) Applicants: CONSORCIO TECNOLOGICO DE SANIDAD ACUICOLA S.A., Santiago (CL); UNIVERSIDAD DE SANTIAGO DE CHILE, Santiago (CL)

(72) Inventors: Mario Cesar Gerardo Tello Reyes, Santiago (CL); Alvaro Eugenio Santibañez Vargas, Santiago (CL); Mick Philippe Parra Mardonez, Santiago (CL); Diego Enrique Paine Cabrera, Santiago (CL); Claudia Andrea Zapata Rojas, Santiago (CL); Andrea Del Pilar Garces Fernandez, Santiago (CL)

(73) Assignees: CONSORICO TECNOLOGICO DE SANIDAD ACUICOLA S.A., Santiago (CL); UNIVERSIDAD DE SANTIAGO DE CHILE, Santiago (CL)

( * ) Notice: Subject to any disclaimer, the term of this patent is extended or adjusted under 35 U.S.C. 154(b) by 0 days.

(21) Appl. No.: 18/467,280

(22) Filed: Sep. 14, 2023

(65) Prior Publication Data

US 2024/0131088 A1    Apr. 25, 2024

Related U.S. Application Data

(62) Division of application No. 16/764,356, filed as application No. PCT/CL2018/050021 on Apr. 20, 2018.

(30) Foreign Application Priority Data

Nov. 14, 2017    (CL) .................................. 2897-2017

(51) Int. Cl.
    A61K 35/744    (2015.01)
    A23K 10/18    (2016.01)
    (Continued)

(52) U.S. Cl.
    CPC ............ *A61K 35/744* (2013.01); *A23K 10/18* (2016.05); *A23K 50/80* (2016.05); *A61K 9/0053* (2013.01);
    (Continued)

(58) Field of Classification Search
    CPC .... A61K 38/217; C12N 1/205; C12N 15/746; C12N 2800/101; A23V 2400/231; C12R 2001/46
    See application file for complete search history.

(56) References Cited

FOREIGN PATENT DOCUMENTS

| CH | 2017-002897 | 11/2017 |
|---|---|---|
| JP | 2006265181 A | 10/2006 |

(Continued)

OTHER PUBLICATIONS

Bermúdez-Humarán, Luis G., et al. "Production of biological active murine IFN-γ by recombinant *Lactococcus lactis*." FEMS microbiology letters 280.2 (2008): 144-149. (Year: 2008).*

(Continued)

*Primary Examiner* — Louise W Humphrey
*Assistant Examiner* — Candice Lee Swift
(74) *Attorney, Agent, or Firm* — Frank Gao, Esq.

(57) ABSTRACT

The present invention falls within the technical field of aquaculture, and specifically, the invention relates to a specific solution for preventing and treating bacterial diseases using a *Lactococcus lactis* lactic acid bacterium trans- (Continued)

formed to produce an interferon type II (IFN II) immunostimulating cytokine, particularly interferon gamma (IFNg or IFNγ). Said transformed bacterium has been deposited in the Chilean Microbial Genetic Resources Collection at INIA with accession number RGM 2416 dated 22 Oct. 2017.

1 Claim, 33 Drawing Sheets

Specification includes a Sequence Listing.

(51) Int. Cl.
| | |
|---|---|
| A23K 50/80 | (2016.01) |
| A61K 9/00 | (2006.01) |
| A61K 38/21 | (2006.01) |
| C12N 1/20 | (2006.01) |
| C12N 15/74 | (2006.01) |
| C12R 1/46 | (2006.01) |

(52) U.S. Cl.
CPC ............ *A61K 38/217* (2013.01); *C12N 1/205* (2021.05); *C12N 15/746* (2013.01); *A23V 2400/231* (2023.08); *C12N 2800/101* (2013.01); *C12R 2001/46* (2021.05)

(56) References Cited

FOREIGN PATENT DOCUMENTS

| WO | 2012/088621 A2 | 7/2012 |
|---|---|---|
| WO | 2014/040987 A1 | 3/2014 |
| WO | 2014/118385 A1 | 8/2014 |
| WO | 2016/037296 A1 | 3/2016 |

OTHER PUBLICATIONS

Zou, Jun, and Christopher J. Secombes. "Teleost fish interferons and their role in immunity." Developmental & Comparative Immunology 35.12 (2011):1376-1387. (Year: 2011).*
Zhu, Duolong, et al. "Isolation of strong constitutive promoters from *Lactococcus lactis* subsp. lactis N8." FEMS microbiology letters 362.16 (2015): fnv107. (Year: 2015).*
Neef, Jolanda, et al. "Versatile vector suite for the extracytoplasmic production and purification of heterologous His-tagged proteins in *Lactococcus lactis*." Applied microbiology and biotechnology 99 (2015): 9037-9048. (Year: 2015).*
Feizollahzadeh, Sadegh, et al. "Expression of biologically active murine interleukin-18 in *Lactococcus lactis*." FEMS Microbiology Letters 363.21 (2016): fnw234. (Year: 2016).*
Takara; https://www.takarabio.com/about/bioview-blog/tips-and-troubleshooting/when-your-his-tagged-constructs-dont-bind; accessed Aug. 26, 2024 (Year: 2018).*
Cooper et al., The Cell: A Molecular Approach. 2nd edition. Sunderland (MA): Sinauer Associates; 2000. The Complexity of Eukaryotic Genomes (Year: 2000).*
Biology Online Dictionary; https://www.biologyonline.com/dictionary/cohesive-end; accessed Aug. 27, 2024 (Year: 2021).*
Addgene1; https://www.addgene.org/protocols/subcloning/; accessed Aug. 26, 2024 (Year: 2017).*
Addgene2; https://www.addgene.org/protocols/restriction-digest/; accessed Aug. 27, 2024 (Year: 2016).*
New England Biolabs; https://www.neb.com/en-us/nebinspired-blog/8-tips-to-follow-when-choosing-a-restriction-enzyme-for-in-vitro-mrna-transcription-for-vaccine-production#:~: text=Restriction%20enzymes%20are%20used%20to,to%20the%20highest%20quality%20standards.; accessed Aug. 27, 2024 (Year: 2021).*
Saraswat, Mayank, Ralph S. Grand, and Wayne M. Patrick. "Desalting DNA by drop dialysis increases library size upon transformation." Bioscience, biotechnology, and biochemistry 77.2 (2013): 402-404. (Year: 2013).*
SNAPGENE: https://www.snapgene.com/guides/restriction-enzyme-cloning: accessed Oct. 6, 2023 (Year: 2023).
GenBank: FJ263446.1:https://www.ncbi.nim.nih.gov/nuccore/FJ263446.1:accessed Jan. 25, 2024 (Year: 2009).
Bermudez-Humaran, Luis G., et al.; "Production of biological active murine IFN-y by recombinant Lactococcus Lactis", FEMS microbiology letters 280.2 (2008): 144-149. (Year): 2008.
The Extended European Search Report dated Sep. 24, 2021; Appln. No. 18878202.3.
Thelvia I. Ramos, et al; "Forms and Methods for Interferon's Encapsulation", Pharmaceutics 2021, 13: 31 pages.
Pedro Berraondo, et al.; "Cytokines in clinical cancer immunotherapy", British Journal of Cancer, (2019) 120: published online: Nov. 9, 2018, 10 pages.
Shu-Jun Cao, et al; "Nanoparticles: Oral Delivery for Protein and Peptide Drugs", AAPS PharmSciTech (2019) 20:190; Published online May 20, 2019, 11 pages.
Husam M Younes, et al; "Interferon-g Therapy: Evaluation of Routes of Administration and Delivery Systems", Journal of Pharmaceutical Sciences, vol. 91, No. 1, Jan. 2022, 16 pages.
Tina Svingerud, et al; "Atlantic Salmon Type I Ifn Subtypes Show Differences in Antiviral Activity and Cell-Dependent Expression: Evidence for High IFNb/IFNc-Producing Cells in Fish Lymphoid Tissues", The Journal of Immunology: Dec. 15, 2012, 189(12): pp. 5912-5923.
Alvaro Santibanez, et al; "Oral Administraction of Lactococcus lactis Producing Interferon Type II, Enhances the Immune Response Against Bacterial Pathogens in Rainbow Trout", Frontiers in Immunology, published Jun. 25, 2021; vol. 12, 12 pages.
USPTO NFOA Dated Feb. 2, 2024 in connection with U.S. Appl. No. 16/764,356.
USPTO FOA dated Jun. 27, 2024 in connection with U.S. Appl. No. 16/764,356.
USPTO FOA dated Oct. 16, 2023 in connection with U.S. Appl. No. 16/764,356.
USPTO NFOA dated Jun. 29, 2023 in connection with U.S. Appl. No. 16/764,356.
Prithy Rupa, et al; "Expression of bioactive porcine interferon-gamma by recombinant Lactococcus lactis", Veterinary Microbiology 129 (2008) 197-202.
Sadegh Feizollahzadeh, et al; "Expression of biologically active murine interleukin-18 in Lactococcus lactis" FEMS Microbiology Letters, 363, 2016; 6 pages.
Jun Zou, et al; "Teleost fish interferons and their role in immunity", Developmental and Comparative Immunology 35 (2011) 1376-1387.
Adelene Ai-Lian Song, et al.; A review on Lactococcus lactis: from food to factory; Microb Cell Fact (2017) 16:55.
S.K. Nayak; "Probiotics and immunity: A fish perspective", Fish & Shellfish Immunology 29 (2010) 2-14.
The Written Opinion PCT/CL2018/050021; mailed Jul. 31, 2018.
International Search Report PCT/CL2018/050021; mailed Jul. 31, 2018.

\* cited by examiner

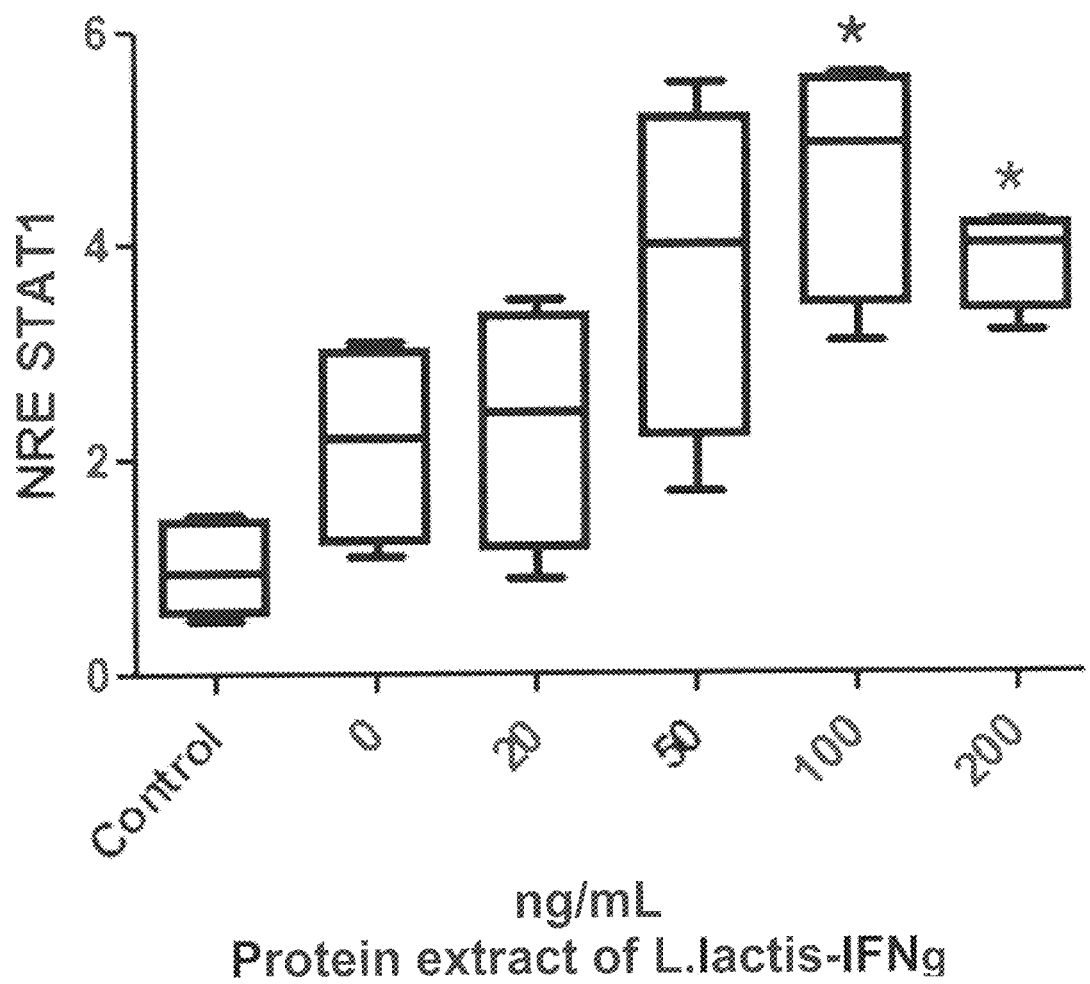
Figura 5a

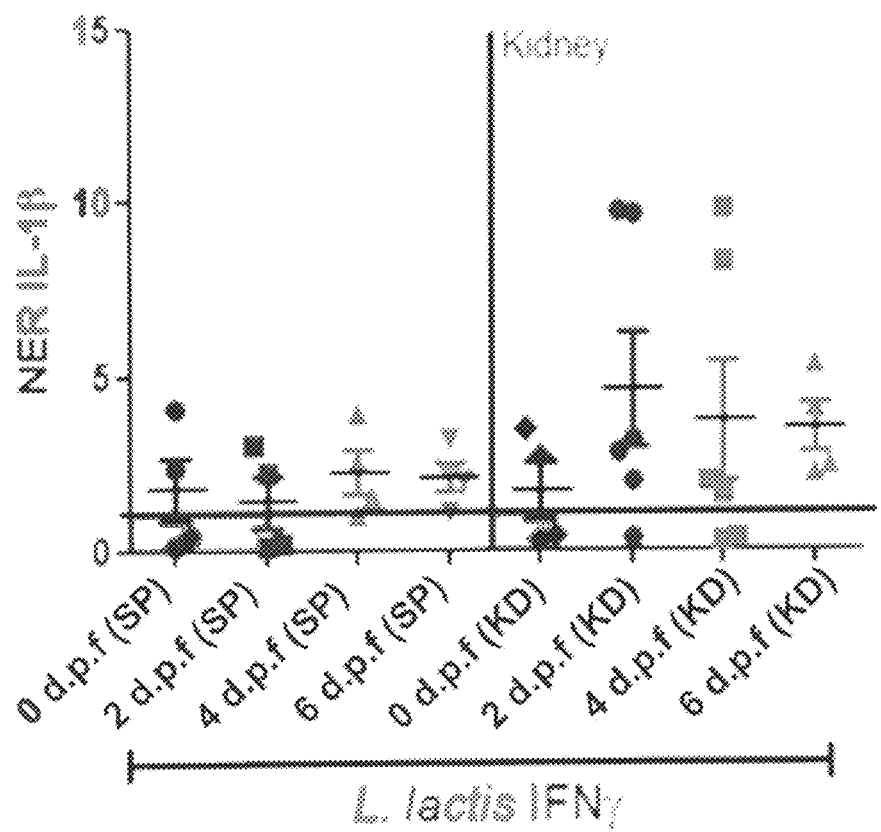
Figura 7a

METHOD FOR PREPARING A TRANSFORMED, *SALMO SALAR* INTERFERON GAMMA (IFNG)-PRODUCING *LACTOCOCCUS LACTIS* BACTERIUM

CROSS-REFERENCES TO RELATED APPLICATIONS

This application is a divisional patent application of U.S. patent application Ser. No. 16/764,356, filed on May 14, 2020, which is a national stage entry of PCT/CL2018/050021, filed on Apr. 20, 2018, all of which are hereby incorporated by reference in their entireties.

AN INCORPORATION BY REFERENCE STATEMENT REGARDING THE MATERIAL IN

An XML file for a "Sequence Listing XML" (see § 1.831(a), submitted via the USPTO patent electronic filing system, identifying
the name of the file: DNA Sequence for CU-76114;
the date of creation of each file: Friday, Dec. 29, 2023
and the size of each file in bytes 36,846 bytes.

FIELD OF INVENTION

The invention belongs to the field of aquaculture, and in particular discloses a solution for preventing and treating bacterial diseases using a transformed lactic acid bacteria to produce an immunostimulant cytokine type II interferon (IFN II), particularly Interferon gamma (IFNg or IFNγ). This transformed bacteria was deposited into INIA's Chilean Collection of Microbial Genetic Resources and has been assigned the accession number RGM 2416, dated Oct. 22, 2017. Likewise, the invention relates to an immunostimulant feed for aquatic species that comprises the transformed lactic bacteria with salmonid type II Interferon. Also concerns the preparation of the probiotic feed, the preparation method of the IFNγ expressing lactic bacteria i.e., the preparation of a cytokine that stimulates antibacterial immune response and an immunomodulator kit against bacterial infections for aquatic species.

BACKGROUND OF THE INVENTION

In salmon farming, different natural causes produce fish mortality, being those of infectious origin the most aggravating. Some of the pathogens that have caused biggest losses are bacteria *Flavobacterium psycrophilum* and *Piscirickesia salmonis*. The main strategy to stimulate fish immune response in aquaculture is by using injectable vaccines. However, this type of immunization involves manipulation and causes high stress to fishes. Furthermore, due to fish's short immune memory continuous boosters are needed, which require manipulation, promoting further stress, mortality and reducing the quality of the fillet. Moreover, oral vaccination and immersion strategies have limited effectivity and its use has restrictions.

Together with the current state of available vaccines, diseases of bacterial origin, mainly those caused by *P. salmonis*, have not been controlled using vaccines which has led to the excessive use of broad spectrum antibiotics, which can impact the environment around fish cages, can increase antibiotic resistance of pathogens and alter fish microbiome. These drawbacks push the need for the creation of new non-invasive methods to stimulate fish immune response. Current research is focused in oral vaccines that can be used as boosters, allowing repetitive immune stimulations without the need of manipulating until harvest.

Interferon are a group of cytokines that were originally discovered due to their antiviral properties (Isaacs and Lindenmann, 1957). In mammals, these cytokines can be classified into three families according to their homology, receptors, structure and function (Pestka et al., 2004). Type I and II interferons are families of multiple genes (17 for type I and 4 for type II) strongly induced by virus, and have an important role controlling viral infections (Lazear et al., 2015, McNab et al., 2015, Teijaro, 2016).

Type II interferon or Interferon gamma (IFNγ) is an immunoregulatory cytokine coded by one gene, produced mainly by NK cells and activated T cells, although it is also secreted by B cells and antigen-presenting cells (APC) (Frucht et al. 2001, Kearney et al., 2013, Zimonjic et al., 1995).

Type I interferon from *Salmo salar* (Atlantic salmon) has shown antiviral properties that induce the expression of several antiviral genes, among these Mx (Ooi et al., 2008, Martin et al., 2007, C. Xu, Evensen and Munang'andu 2015). In vitro and in vivo experiments have shown that type I interferon is effective against pathogens of economic relevance such as IPNV, IHNV, ISAV and SAV (Chang et al., 2014, 2016, Robertsen et al., 2003, Saint-Jean and Pérez-Prieto, 2006, Sun et al., 2011, Svingerud et al., 2012, 2013, Xu et al., 2010). Furthermore, type I interferon in *Salmo salar* also stimulates adaptative immunity, increasing immunostimulation produced by DNA vaccines (Chang et al., 2015).

However, bioactivity assays using recombinant *Salmo salar* or rainbow trout IFNg have shown that this cytokine is capable of inducing the expression of MHCI and MHCII proteins, which are involved in the processing of antigens and increasing the respiratory burst of phagocytic cells (Martin et al., 2007a, 2007b, 2007c, Zou et al., 2005). Additionally, IFNg has shown antiviral properties in vitro against SAV and IPNV (Sun et al., 2011).

As in human beings, IFNs have the potential to be used in salmon farming as therapeutics or in prophylaxis treatments against virus. However, the use of these cytokines has been unsuccessful in aquaculture, mainly due to lack of an appropriate vehicle, compatible with fish physiology that makes its use effective.

The present invention relates to the development of bacteria to be used as an oral immunostimulant for non-specific stimulation of the innate response against bacterial infections, of either intracellular or extracellular pathogens. The present invention shows that salmon IFN gamma (IFNγ) confers protection against bacterial infections in salmonids by activating genes that increase cellular and humoral immune response of fish. Therefore, expression of the immunostimulant cytokine in the mucus membrane, using acid lactic bacteria as liberation vehicle, confers a protective effect on fish against bacterial infections.

In the last decades, lactic acid bacteria (LAB) have emerged as a feasible vehicle for in situ liberation of cytokines and bioactive peptides within the gastrointestinal tract of mammals (Bahey-El-Din et al., 2010; Steidler et al., 2009). Interferons alpha (Bayat et al., 2014, Ma et al., 2014, Zhang et al., 2010), beta (Zhuang et al., 2008), gamma (Bermudez-Hunnaran et al., 2008; Rupa et al., 2008) and IL-10 (Steidler et al., 2000) have been successfully expressed in LAB maintaining their biological active form, producing local and systemic effects after being administrated to mammals.

Although use of *Lactococcus lactis* strains for delivery of recombinant proteins, such as antigenic proteins, cytokines, including IFN, or other biological active proteins in animals has been previously reported by Zhuang Z, Wu ZG, Chen M, Wang PG. (2008), Bahey-El-Din M, Gahan CG. (2011), WO2011150127, WO2010139195, CN102329766, CN102796755, CL201503797, CN104120142, CN103074291, US4808523, CN105331570 or WO2014040987, the present invention describes a specific solution, of a specific LAB bacteria, to prepare immunomodulating feed to target an unresolved problem in aquaculture, such as bacterial diseases, specifically salmonid diseases in salmon farming.

The use of LAB for in situ delivery of bioactive proteins in Atlantic salmon and rainbow trout has been poorly studied, only exploring its use for delivery of antigenic peptides (Li et al., 2012). The inventors have previously described transformation of *Lactococcus lactis* bacteria with type I interferon, which proved to be useful preventing the viral disease Infectious Pancreatic Necrosis. However, the present invention describes a strain of *Lactococcus lactis* transformed with type II IFN that surprisingly could protect fish against bacterial diseases important to aquaculture, specifically salmons. In this invention *Lactococcus lactis* was used for expressing IFNg from *Salmo salar*. Lactic bacteria expressing *Salmo salar* IFNg used in this invention, when administrated with feed, were biologically functional in in vivo testing, protecting against bacterial diseases. Moreover, administration of this modified LAB shows that treated fish can effectively control bacterial infections of intracellular and extracellular pathogens such as *Flavobacterium psycrophilum* or *Piscirickesia salmonis*, which could not have been foreseen or deduced directly from the state of the art.

SUMMARY OF THE INVENTION

The present invention relates to transformed *Lactococcus lactis* bacteria producing interferon gamma (IFNg) from *Salmo salar* that comprises the *Lactococcus lactis* NZ3900 strain that comprises the genetic expression system than comprises the DNA construction pNZ8149-p1-USP45-IFNg-GGG-6xHIS. These transformed *Lactococcus lactis* bacteria has been assigned the accession number RGM 2416, dated Oct. 22, 2017, into INIA's Chilean Collection of Microbial Genetic Resources. Likewise, the invention relates to a plasmid to transform *L. lactic* bacteria to produce interferon gamma (IFNγ) that comprises the vector pNZ8149 and the DNA sequence P1-USP45-IFNγ-GGG-6× HIS and to the method to prepare the previously stated transformed *L. lactis* bacteria. It is also part of the invention the probiotic feed to immunostimulate fish which comprises transformed *L. lactis* bacteria with the objective to prevent or treat bacterial infections in fish and the preparation of the feed that comprises mixing the transformed bacteria with fish feed. Furthermore, the invention comprises a fish immunomodulatory composition and a kit that comprises the transformed *L. lactis* bacteria. Moreover, the invention describes the use of the transformed *L. lactis* bacteria to prepare feed to immunostimulate fish, to reduce bacterial load, preferably of pathogenic bacteria of fish such as *Flavobacterium psychrophilum* and/or *Piscirickettsia salmonis*.

DESCRIPTION OF THE FIGURES

FIG. 5a shows induction of STAT1 of genes related to immune response of SHK-1 cells activated by a sample of sonicated lysate of *L. lactis*-IFNγ. Different concentrations of samples from mixtures of *L. lactis* lysates, as presented in Table 1, were used. Lysates were added to SHK-1 cultures for 8 hours at 16° C. Afterwards, induction of STAT1, gamma IP-10, IFNγ, TGF-b, IL-1b and IL-6 was quantified. Obtained values were normalized against eF1a expression. Control: SHK-1 cells without treatment. 0: SHK-1 cell cultures supplemented with 200 ng/ml of *L. lactis* without insert (IFNγ) extract. 20, 50, 100 and 200: SHK-1 cell cultures supplemented with 0 ng/ml, 20 ng/ml, 50 ng/ml, 100 ng/ml and 200 ng/mL of sonicated extract of *L. lactis*-IFNγ respectively. The assay was performed with biological and technical duplicates.

FIG. 7*a* shows RT-qPCR quantification of mRNA related to immune response of interferon gamma (IFNγ) during feeding of *Lactococcus lactis*-IFNγ to rainbow trout. Relative quantification was performed to different genes that responded to IFNγ. Spleen (SP) and kidney (KD) simples were studied at day 0, 2, 4 and 6 during probiotic feeding (d.p.f) Relative expression of IL-1b was performed normalizing against eF1a. One-tailed Mann-Whitney analysis was performed, and significance was determined by t-student ($p<0.05$) comparing expression levels to those observed on day 0 before probiotic feeding. NER: Normalized relative expression. Finally, 3 fish were sampled from each group at all timepoints and all assays were performed in technical duplicates.

DETAILED DESCRIPTION

Figure 1:
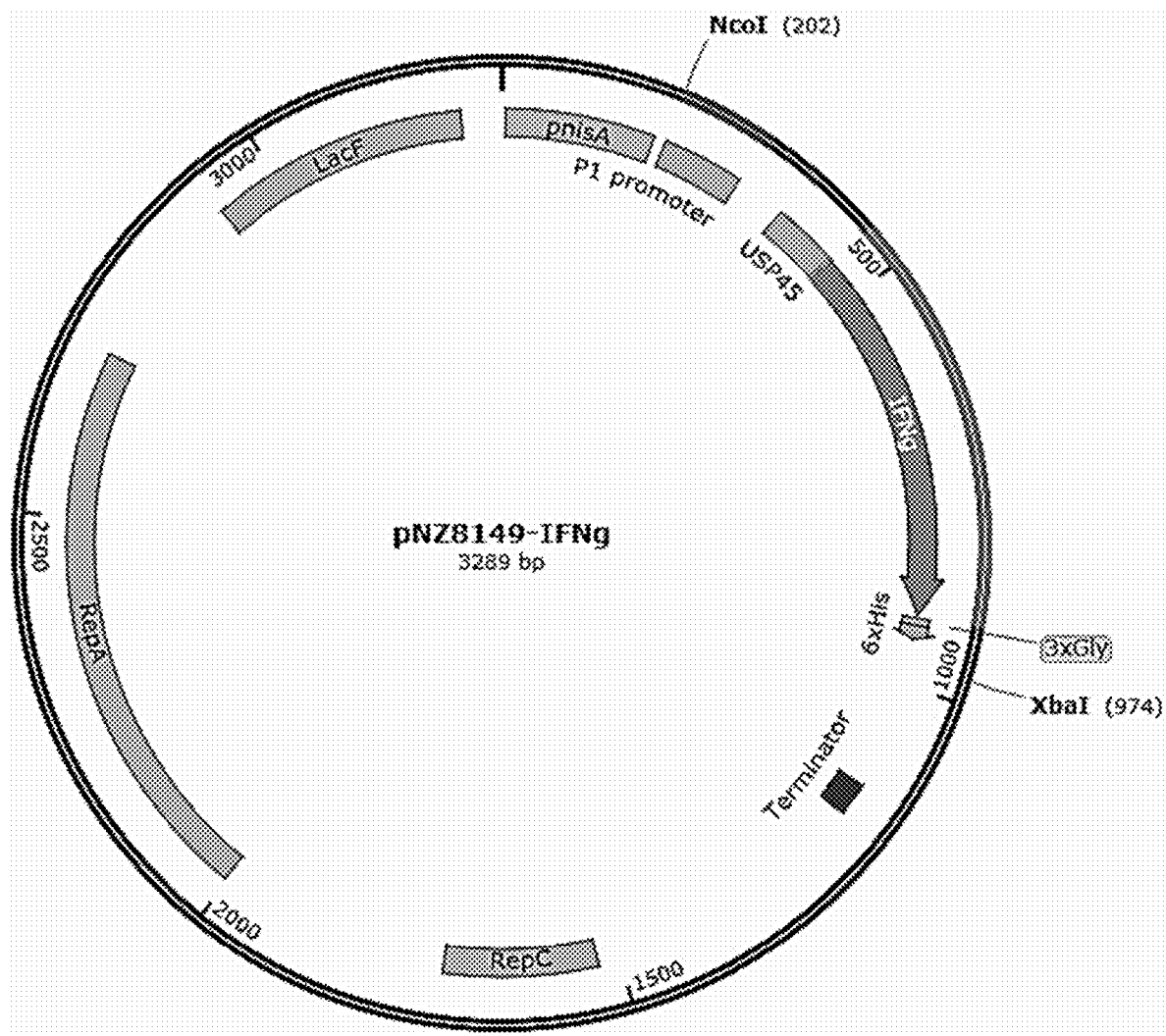
FIG. 1. Genetic map of the pNZ8149-IFNg construction. PnisA: nisin-inducible promoter. P1: *L. lactis* constitutive expression promoter. Usp45: secretion signal. IFNγ: *Salmo salar* interferon gamma (IFNγ) mature mRNA coding sequence. 3× Gly: sequence coding for three glycines. 6×His: histidine tail. RepA and RepC: replication genes. LacF: lactase coding gene. NcoI and XbaI restriction sites are shown, these were used to clone the cassette into vector pNZ8149. Plasmid size: 3289 bp.

The present invention refers to a probiotic feed that comprises lactic acid bacteria, particularly *L. lactis*, transformed to produce an immunostimulant cytokine, preferably type II IFN, to immunostimulate aquatic species against bacterial infections, thus achieving heterologous expression of an immunostimulant protein of *Salmo salar* in lactic acid bacteria. The *L. lactis* bacteria has been assigned the accession number RGM 2416, dated Oct. 22, 2017, by the INIA's Chilean Collection of Microbial Genetic Resources, Chile.

Immunostimulant proteins strongly regulate immune response. Administration of recombinant immunostimulant proteins have allowed their use as a therapeutic to increase immune response against bacterial pathogens. In aquaculture, there are no available in situ heterologous production systems for functional immunostimulant proteins for therapeutic use. Lactic acid bacteria are GRAS (Generally Regarded as Safe) organisms, that because of this classification have been used as vaccines and as therapeutic release systems.

The lactic acid bacteria of this invention can be used to express and secrete functional immunostimulant proteins in aquatic species, particularly in fishes and preferably in *Salmo salar* and rainbow trout. The present lactic acid bacteria allows non-invasive immunogenic protection applicable in large scale, capable of increasing current immunization systems.

Administration of the present lactic acid bacteria, that produce an immunostimulant cytokine, can stimulate in vivo the expression of genes that respond to IFN gamma and reduce mortality of aquatic species challenged with *F. psychropillhum* and *P. salmonis*

Using molecular biology tools, lactic acid bacteria was generated that produce an immunostimulant cytokine. Its immunostimulant properties were studied in species highly important for aquaculture, administrating an oral dosage of $1\times10^7$ UFC per fish. Immunostimulation was assessed quantifying genes that respond to this cytokine using real time qPCR normalizing their expression against the housekeeping gene eF1a. To achieve this objective, total RNA was extracted from immunological organs (spleen and kidney), which were previously assessed studying their morphology and any signs of toxicity. The lactic acid bacteria produce and secret the heterologous protein. The protein was located mainly in the cytoplasmatic fraction. The bioassays showed that the protein is functional when stimulating the expression of immunological genes.

The invention relates, particularly, to transformed *Lactococcus lactis* bacteria that produce interferon gamma from *Salmo salar* that includes the DNA construction that comprises pNZ8149-P1-USP45-IFNg-GGG-6×HIS where pNZ8149 is the transformed vector; P1 is *L. lactis* constitutive expression promoter; Usp45 is a secretion signal; IFNγ is *Salmo salar* interferon gamma (IFNγ) mature mRNA coding sequence; GGG is a sequence coding for three glycines and 6×His is s sequence coding for 6 terminal histidines. The transformed strain of *Lacococcus lactis* is identified as NZ3900, however, it is not limiting and other strains of *L. lactis* could be used. The bacteria is preferably *Lactococcus lactis* NZ3900 transformed with the genetic system that comprises the plasmid pNZ8149/P1-USP45-IFNg-GGG-6×HIS. Preferably, the recombinant strain is the one with the accession number RGM 2416, dated Oct. 22, 2017, by the INIA's Chilean Collection of Microbial Genetic Resources, Chile.

It is also part of the invention, a useful plasmid to transform *L. lactis* bacteria to produce interferon gamma (IFNγ) that comprising the vector pNZ8149 and the sequence P1-Usp45-IFNγ-GGG-6×HIS; where P1 is *L. lactis* constitutive expression promoter; Usp45 is a secretion signal; IFNγ is *Salmo salar* interferon gamma (IFNγ) mature mRNA coding sequence; GGG is a sequence coding for three glycines and 6×His is s sequence coding for 6 terminal histidines. Likewise, the invention relates to a method to prepare the transformed *L. lactis* bacteria that comprises the following steps:

a) Digesting with restriction enzymes a plasmid that contains the reading frame of *Salmo salar* IFNg codon optimized for *Lactococcus lactis,* b) purifying the digestion product, corresponding to the IFNg gene with sticky ends for restriction enzymes, c) Meanwhile, digesting with the same enzymes the plasmid NZ8149, d) Purifying the linearized plasmid from an agarose gel, e) Ligating both purified products with ligase, f) Dialyzing the ligation product, g) Transforming electrocompetent *L. lactis* bacteria with the ligated plasmid.

The restriction enzymes are preferably, for steps a) and c) restriction enzymes NcoI and XbaI and electrocompetent bacteria of step g) is the strain *L. lactis* NZ3900.

It is part of this invention a probiotic feed to immunostimulate aquatic species, preferably immunostimulate fishes. The probiotic feed comprises transformed *L. lactis* bacteria with a transformed *Lactococcus lactis* bacteria producing interferon gamma of *Salmo salar* that includes the DNA construction that comprises pNZ8149-P1-USP45-IFNg-GGG-6×HIS where pNZ8149 is the transformed vector; P1 is *L. lactis* constitutive expression promoter; Usp45 is a secretion signal; IFNγ is *Salmo salar* interferon gamma (IFNγ) mature mRNA coding sequence; GGG is a sequence coding for three glycines and 6×His is s sequence coding for 6 terminal histidines. Likewise, the invention comprises the method to prepare the probiotic feed described above.

Additionally, this invention protects any immunomodulatory composition for aquatic species, under the broadest scope of composition. The composition can be liquid or solid and have excipients to provide stability for storage and enhance bioavailability of the transformed bacteria of this invention. Furthermore, the composition includes all combinations of useful organic molecules to administrate to aquatic species such as proteins, lipids, saccharides, in combination with the transformed *L. lactis* bacteria described above or with the bacteria described in the preferred conducted examples. This composition can comprise the combination of the bacteria of the invention with recombinant protein vaccines or with nucleic acid vaccines, bacterines, probiotics, prebiotics or other immunomodulators, vitamins, etc.

The use of the transformed *L. lactis* bacteria is for preparing feed or a useful composition for immunostimulating aquatic species, particularly, to immunostimulate fishes. The given use for these bacteria is to prepare useful feed to reduce bacterial load, preferably bacterial load of *Flavobacterium psychrophilum* and or *Piscirickettsia sal-* monis. The use of the bacteria and the feed that comprises it is to prepare a feed or a useful composition to treat or prevent infection from *Flavobacterium psychrophilum* and/or *Piscirickettsia salmonis* in fishes.

Is part of this invention, a kit that includes a packing that comprises the transformed *L. lactis* bacteria with the DNA construction pNZ8149-P1-USP45-IFNg-GGG-6×HIS. Likewise, this kit can comprise instructions to be used to feed, treat or prevent bacterial diseases in aquatic species, preferably, fishes important for aquaculture. In the preferred embodiment instructions have information for the use for feeding fishes, treat or prevent diseases caused by *Flavobacterium psychrophilum* and *Piscirickettsia salmonis* in fishes.

The invention also comprises the method to reduce bacterial load in aquatic species, that comprises the administration to this species the feed prepared with transformed *L. lactis* bacteria, selected from any bacteria that comprises the DNA construction pNZ8149-P1-USP45-IFNg-GGG-6×HIS detailed in the examples of this invention. The aquatic species are preferably fishes, and the method treats or prevents infection with *Flavobacterium psychrophilum* or *Piscirickettsia salmonis*. The method for delivery is capable of treating or preventing a bacterial infection by reducing bacterial load in aquatic species, preferably fishes.

EXAMPLES

Example 1

Using synthetic biology the coding gene for a codon-optimized immunostimulating protein from *Salmo salar* with a secretion peptide and 6 histidine tail was designed and synthesized. The gene was clones into a food grade expression vector. Production of the heterologous protein was confirmed using Western Blot and its functionality through bioassays.

The present invention consists in a recombinant *Lactococcus lactis* NZ3900 strain, that comprises the plasmid NZ8149 into which a synthetic DNA segment, that comprises P1 promoter, the signal peptide of protein USP45, a gene that codifies the mature sequence of type I interferon of *Salmo salar* and a tail of 3 glycines and 6 histidines, denominated as pNZ8149-IFNgSS (FIG. 1), was cloned.

Figure 2:
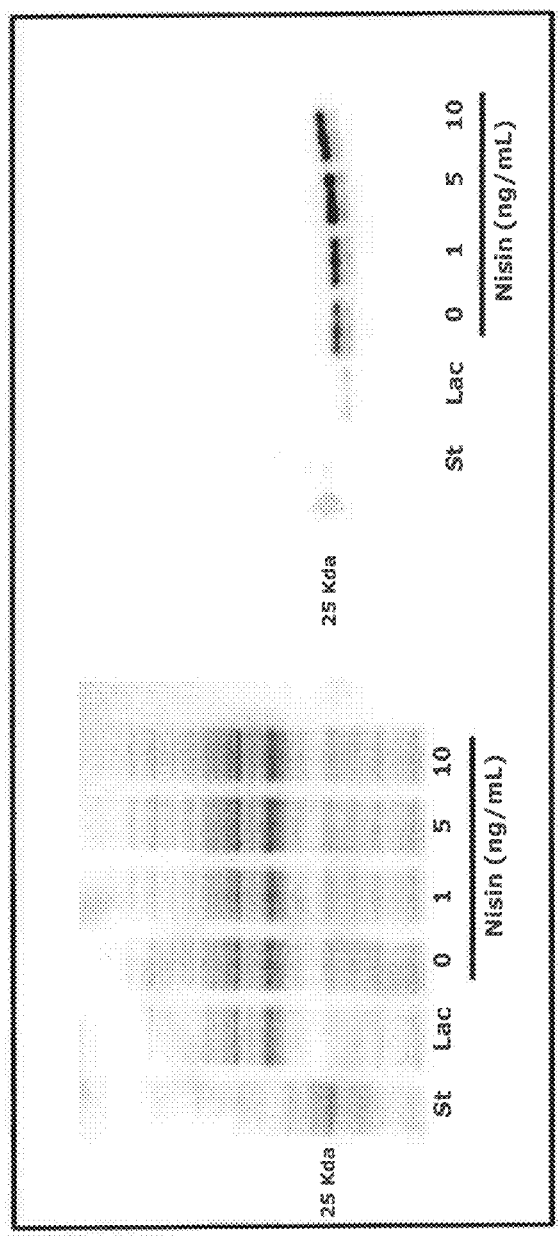
FIG. 2. Detection of IFN gamma from the cytosolic content of recombinant *L. lactis* induced with different concentrations of nisin. St: molecular weight standard. Lac: 20 μg of total protein of recombinant *L. lactis* that contains the pNZ8149 plasmid without the IFNγ gene induced with 10 ng/ml of nisin. 0, 1, 5 and 10:20 ug of total protein of recombinant *L. lactis* that contains the pNZ8149 plasmid with the IFNγ gene induced with 0, 1, 5 and 10 ng/ml of nisin respectively. To the left, a protein gel dyed with Coomassie blue and to the right a Western Blot for histidine tail (6×His) detection. The primary antibody used in the Western Blot targeted histidine tails (1:2000), antibodies were incubated for 1 hour at room temperature while shaking. The secondary antibody conjugated to HRP binds to the primary antibody (1:2000) and was incubated for 1 hour at room temperature while shaking. After incubation with each antibody the membrane was washed 3 times for 10 minutes with PBS-Tween10 0.15%. The membrane was developed using the UltraSIgnal® kit and the chemidock LI-COR equipment.
Figure 3:
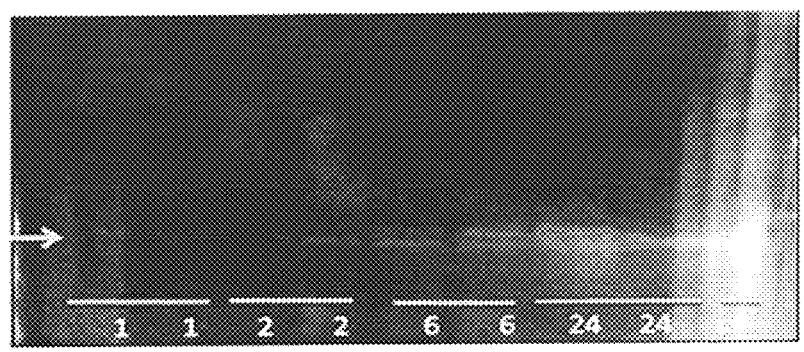
FIG. 3. Secretion kinetics of IFNg produced by *L. lactis*-IFNγ. Four cultures of 40 mL of M17 broth supplemented with lactose were inoculated with 2% of *L. lactis*-IFNγ and incubated at 30° C. without shaking. Supernatant were analyzed at 1, 2 6 and 24 hours after nisin induction. The primary antibody used in the Western Blot targeted histidine tails (1:2000), antibodies were incubated for 1 hour at room temperature while shaking. The secondary antibody conjugated to HRP binds to the primary antibody (1:2000) and was incubated for 1 hour at room temperature while shaking. After incubation with each antibody the membrane was washed 3 times for 10 minutes with PBS-Tween10 0.15%. The membrane was developed using the UltraSIgnal® kit and the chemidock LI-COR equipment. C+: 10 ug of cytoplasmic content. To the left the molecular weight standard, in kDa, can be seen. All samples were loaded in duplicate.
Figure 4:
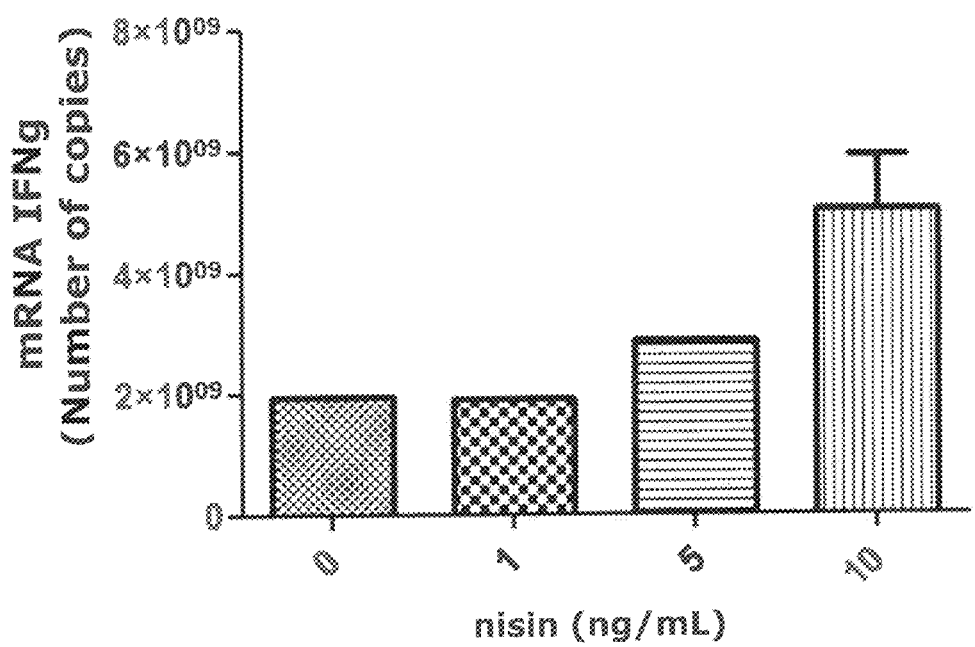
FIG. 4. *L. lactis*-IFNγ IFNγ mRNA copy number quantification using RT-qPCR. Absolute quantification of the number of copies of IFNγ coding mRNA from *L. lactis*-IFNγ cultures induced with different amounts of nisin was performed. Total RNA was extracted using TRIzol from 20 mL of bacterial culture. Afterwards, 100 ng of RNA from each culture were treated with DNase for RT-qPCR. Reverse transcription controls show no amplification (data not shown). The assay was performed with biological and technical duplicates.
Figure 5B:
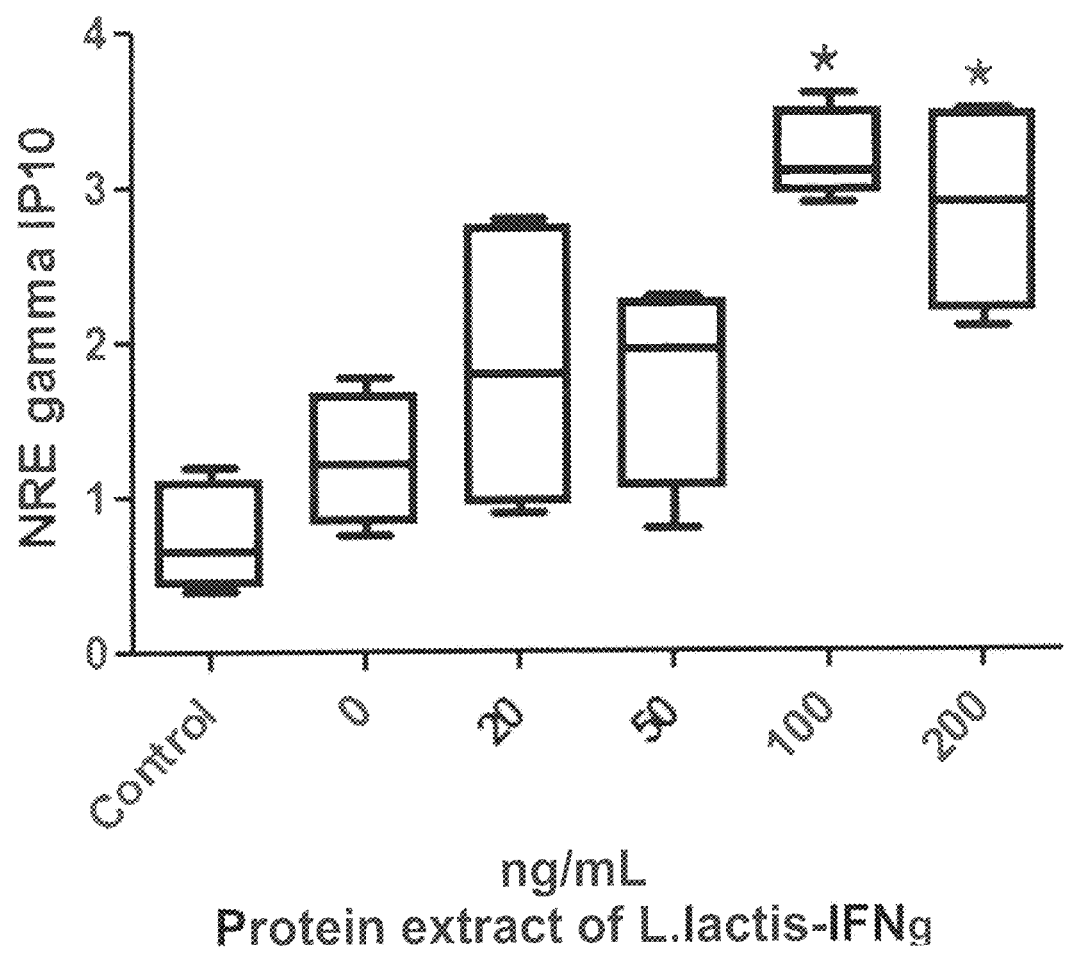
FIG. 5*b* shows induction of gamma IP-10 of genes related to immune response of SHK-1 cells activated by a sample of sonicated lysate of *L. lactis*-IFNγ. Different concentrations of samples from mixtures of *L. lactis* lysates, as presented in Table 1, were used. Lysates were added to SHK-1 cultures for 8 hours at 16° C. Afterwards, induction of STAT1, gamma IP-10, IFNγ, TGF-b, IL-1b and IL-6 was quantified. Obtained values were normalized against eF1a expression. Control: SHK-1 cells without treatment. 0: SHK-1 cell cultures supplemented with 200 ng/ml of *L. lactis* without insert (IFNγ) extract. 20, 50, 100 and 200: SHK-1 cell cultures supplemented with 0 ng/ml, 20 ng/ml, 50 ng/mL, 100 ng/ml and 200 ng/ml of sonicated extract of *L. lactis*-IFNγ respectively. The assay was performed with biological and technical duplicates.
Figure 5C:
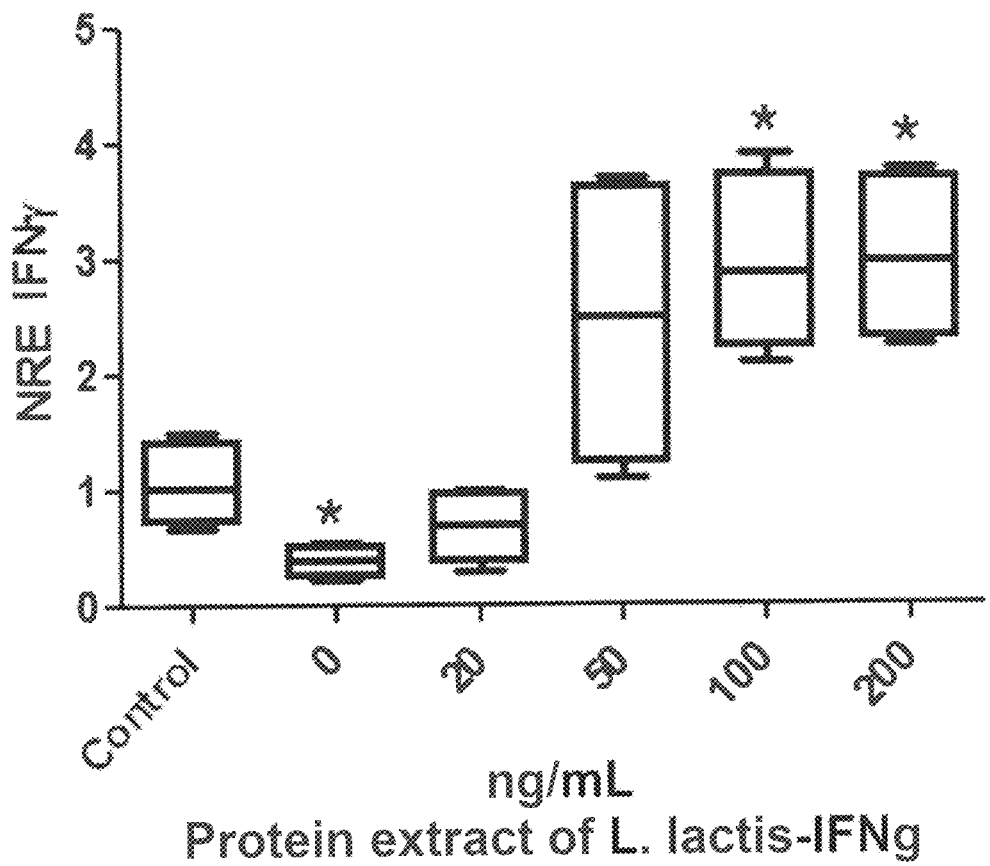
FIG. 5*c* shows induction of IFNγ of genes related to immune response of SHK-1 cells activated by a sample of sonicated lysate of *L. lactis*-IFNγ. Different concentrations of samples from mixtures of *L. lactis* lysates, as presented in Table 1, were used. Lysates were added to SHK-1 cultures for 8 hours at 16° C. Afterwards, induction of STAT1, gamma IP-10, IFNγ, TGF-b, IL-1b and IL-6 was quantified. Obtained values were normalized against eF1a expression. Control: SHK-1 cells without treatment. 0: SHK-1 cell cultures supplemented with 200 ng/ml of *L. lactis* without insert (IFNγ) extract. 20, 50, 100 and 200: SHK-1 cell cultures supplemented with 0 ng/ml, 20 ng/mL, 50 ng/mL, 100 ng/ml and 200 ng/ml of sonicated extract of *L. lactis*-IFNγ respectively. The assay was performed with biological and technical duplicates.
Figure 5D:
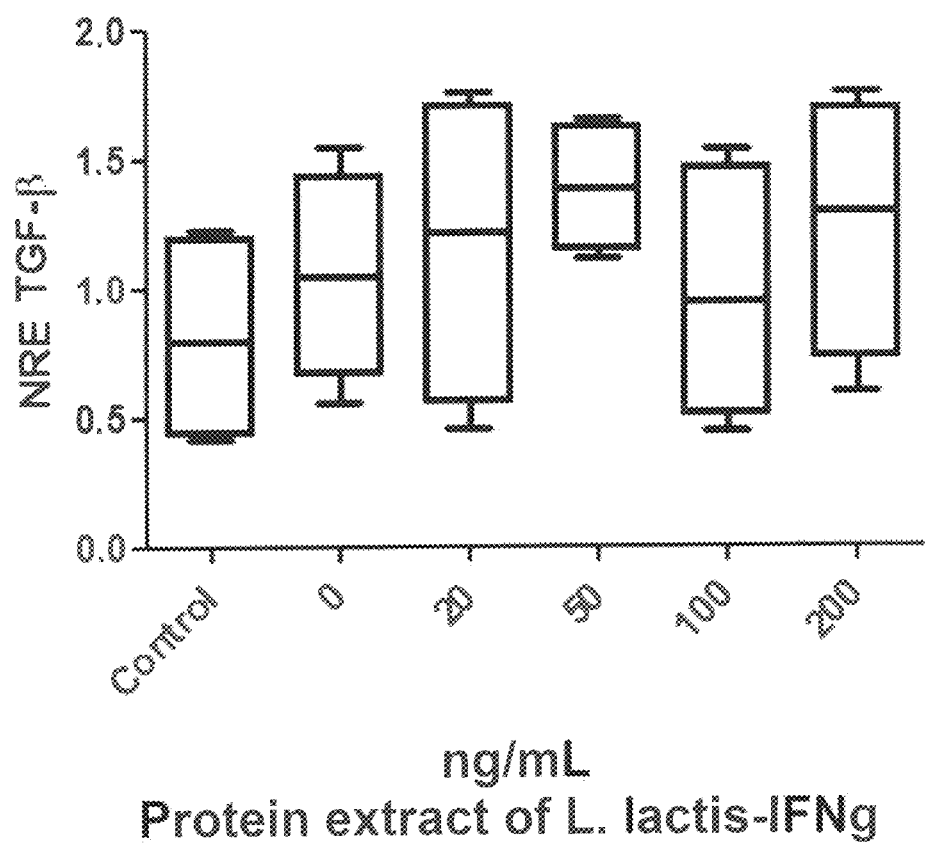
FIG. 5*d* shows induction of TGF-b of genes related to immune response of SHK-1 cells activated by a sample of sonicated lysate of *L. lactis*-IFNγ. Different concentrations of samples from mixtures of *L. lactis* lysates, as presented in Table 1, were used. Lysates were added to SHK-1 cultures for 8 hours at 16° C. Afterwards, induction of STAT1, gamma IP-10, IFNγ, TGF-b, IL-1b and IL-6 was quantified. Obtained values were normalized against eF1a expression. Control: SHK-1 cells without treatment. 0: SHK-1 cell cultures supplemented with 200 ng/ml of *L. lactis* without insert (IFNγ) extract. 20, 50, 100 and 200: SHK-1 cell cultures supplemented with 0 ng/ml, 20 ng/ml, 50 ng/ml, 100 ng/ml and 200 ng/ml of sonicated extract of *L. lactis*-IFNγ respectively. The assay was performed with biological and technical duplicates.
Figure 5E:
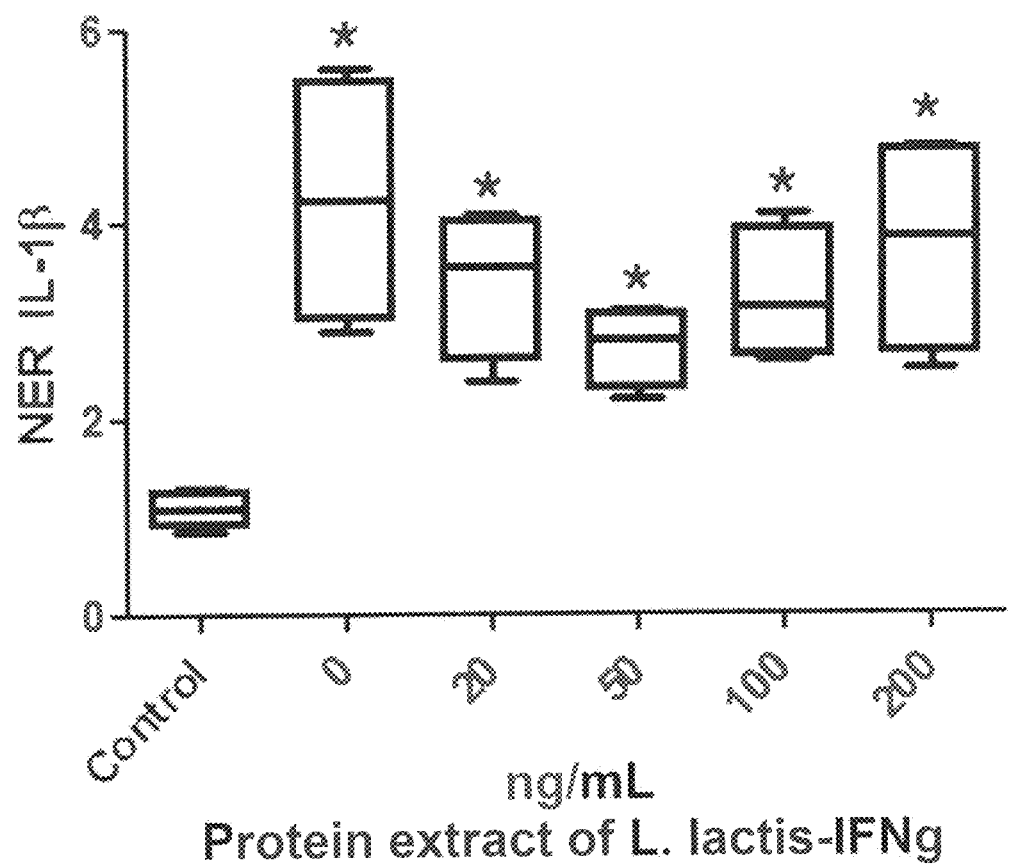
FIG. 5*e* shows induction of IL-1b of genes related to immune response of SHK-1 cells activated by a sample of sonicated lysate of *L. lactis*-IFNγ. Different concentrations of samples from mixtures of *L. lactis* lysates, as presented in Table 1, were used. Lysates were added to SHK-1 cultures for 8 hours at 16° C. Afterwards, induction of STAT1, gamma IP-10, IFNγ, TGF-b, IL-1b and IL-6 was quantified. Obtained values were normalized against eF1a expression. Control: SHK-1 cells without treatment. 0: SHK-1 cell cultures supplemented with 200 ng/ml of *L. lactis* without insert (IFNγ) extract. 20, 50, 100 and 200: SHK-1 cell cultures supplemented with 0 ng/ml, 20 ng/mL, 50 ng/mL, 100 ng/ml and 200 ng/ml of sonicated extract of *L. lactis*-IFNγ respectively. The assay was performed with biological and technical duplicates.
Figure 5F:
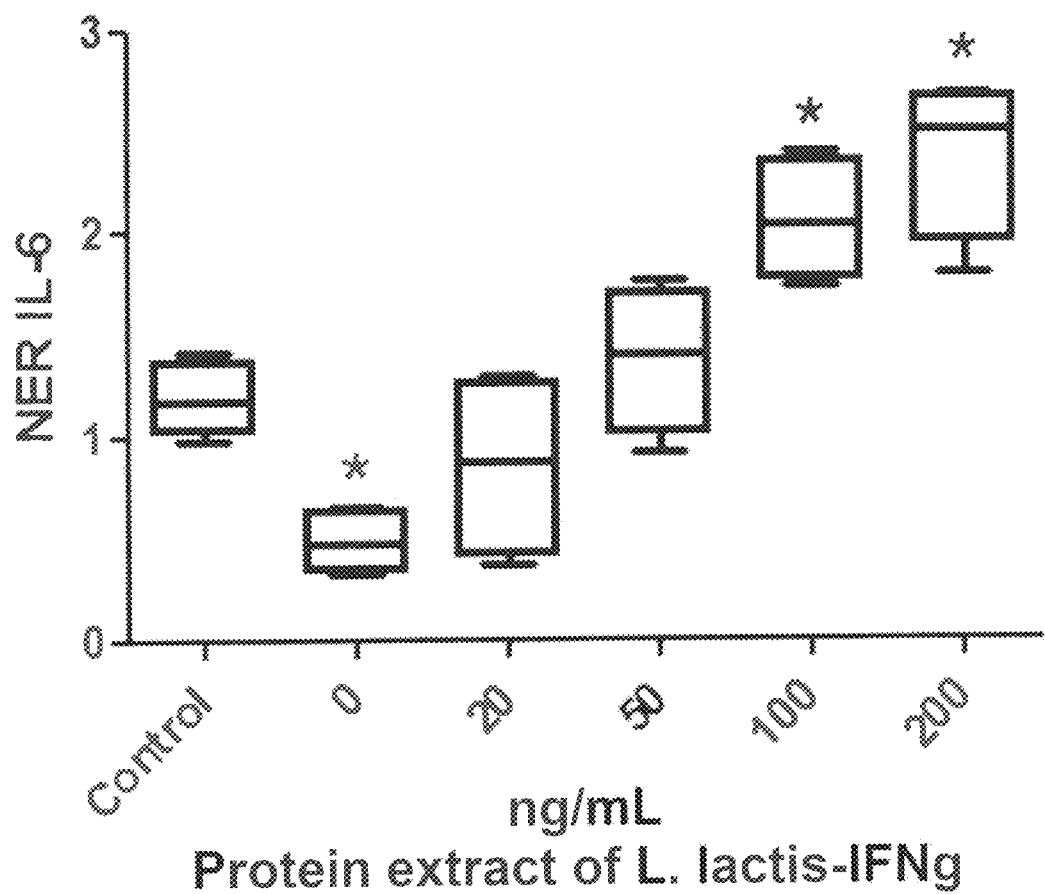
FIG. 5*f* shows induction of IL-6 of genes related to immune response of SHK-1 cells activated by a sample of sonicated lysate of *L. lactis*-IFNγ. Different concentrations of samples from mixtures of *L. lactis* lysates, as presented in Table 1, were used. Lysates were added to SHK-1 cultures for 8 hours at 16° C. Afterwards, induction of STAT1, gamma IP-10, IFNγ, TGF-b, IL-1b and IL-6 was quantified. Obtained values were normalized against eF1a expression. Control: SHK-1 cells without treatment. 0: SHK-1 cell cultures supplemented with 200 ng/ml of *L. lactis* without insert (IFNγ) extract. 20, 50, 100 and 200: SHK-1 cell cultures supplemented with 0 ng/mL, 20 ng/ml, 50 ng/ml, 100 ng/ml and 200 ng/ml of sonicated extract of *L. lactis*-IFNγ respectively. The assay was performed with biological and technical duplicates.

The sequence of the IFNγ gene was obtained from *Salmo salar*'s genome and codon-optimized to be expressed in an *L. lactis* host (FIG. 1). This strain expresses constitutively the IFNγ gene driven by promoter P1, from *L. lactis* sequence SEQ ID No:2, and in inducible by the nisin promoter present in the commercial vector (FIG. 2). IFNγ is secreted to the culture media by the signal peptide Usp45, sequence SEQ ID No 3, that is merged in the reading frame of the IFN gamma sequence, SEQ ID No:4 (FIG. 3). Expression of IFNγ was detected in extracts of IFNγ producing *L. lactis* extract compared to extracts of the strain that contains the pNZ8149 without the gene's reading frame (FIG. 4).

Methodology

Design of the pNZ8149 vector. To design the lactococcal vector, the plasmid pNZ8140 (Mobitec®) was used as backbone and the plasmid pJet1.2-IFNg (Genescript®) contained the reading frame of *Salmo salar*'s IFNγ (GenBank: FJ263446.1). The IFNγ gene was codon-optimized in silico for *Lactococcus lactis* NZ3900 using the online application www.kazusa.or.jp, and then modified to include in the amino terminal end the sequence that codifies the USP45 peptide and in the carboxylic end a sequence that codifies a tail of 3 glycines and 6 histidines (GGGHHHHHH) SEQ ID No:5. These sequences were added in frame with the *L. lactis* codon-optimized IFNγ gene. Likewise, the P1 promoter sequence was added in silico to the 5' end of the sequence that codifies USP45-IFNg-GGGHHHHHH. This new sequence, P1-USP45-IFNg-GGGHHHHHH was synthetized in vitro and cloned into pJet1.2 (Genescript®) (FIG. 1). The identity of the genetic sequence of the construct was corroborated by Sanger sequencing and the amino acid sequence that the gene synthetizes using the web page www.bioinformatics.org.

Because the plasmids pNZ8149 and pJet1.2-IFNγ have a replication origin for propagation in *E. coli* and ampicillin resistance as selection marker, the MC1061 strain was used to obtain high concentrations of both plasmids. Afterwards, both plasmids were digested for 1 hour at 37° C. with enzymes NcoI and XbaI, present in the multiple cloning site of pNZ8149 and in each end of the IFNγ in pJet1.2. Both digestions were corroborated in a 1% w/v agarose gel from which the linear vector and the insert were purified using the Wizard SV Gel and PCR Clean-Up System (Promega®). The vector and the insert were ligated overnight at 4° C. and dialyzed the next day for 30 minutes prior to electroporation with *Lactococcus lactis* NZ3900 to obtain the bacteria with vector pNZ8149-IFNg.

Detection of IFNγ in *L. lactis* cultures. To detect the expression of the recombinant protein, Western Blot assays were performed from cytoplasmatic extract of sonicated *L. lactis*. To do so, a preculture of *L. lactis* pNZ8149-IFNg was cultured overnight at 30° C. in M17 media with 0.5% lactose. The following day, a 40 mL culture was inoculated with 2% inoculum, after cultivating at 30° C. up to an $OD_{600}$ 0.4-0.6 the culture was divided in equal parts. To some cultures, nisin was added between 0 and 10 ng/mL. Cultures were then incubated for 2 hours at 30° C. Afterwards, bacteria were collected through centrifugation at 7,000 RPM for 20 min at 4° C.

The bacterial pellet was resuspended in 500 uL of PBS1× supplemented with a protease inhibitor 1 mM. Afterwards, it was sonicated 5 times for 15 seconds each with an Ultrasonic processor Sonic Vibracell VCX130 (90% amplitude), kept in ice between cycles. The sample was centrifuged at 6,000 RPM for 10 min at 4° C. and the supernatant was separated from the cellular debris, storage in a new tube and frozen at −20° C. until its use.

To determine total protein concentration in the extract the Bradford method was used. Once the concentration was known, it was normalized to resolve and compare the amount of protein through SDS-PAGE electrophoresis. 10 μg of the cytoplasmatic extract of induced and not induced with nisin IFNγ producing *L. lactis* and of *L. lactis* that contained a pNZ8149 plasmid without a IFNγ reading frame as control were loaded. Samples were run in an electrophoresis for 40 min at 60 V and then for 1.5 hr at 120 V. Proteins contained in the polyacrylamide gel were transferred to a nitrocellulose membrane at 300 mA for 7 min. Afterwards, the membrane was blocked with a PBS-BSA 2% solution while shaking at 4° C. Then, the membrane was washed at room temperature 3 times for 10 minutes with PBS 1×-Tween 20 at 0.1% and incubated for 1 hour with an anti-His primary antibody at a 1:2,000 dilution in a 2% PBS-BSA solution. Next, the membrane was washed with the same procedure and then incubated for 1 hour with a 1:5,000 dilution of the secondary antibody, an anti-rabbit IgG conjugated with horseradish peroxidase. The membrane was washed again and developed by chemiluminescence with the Supersignal® West Pico Chemiluminescent Substrate Kit, incubating the solutions for 5 minutes and exposing the membrane and a digital development equipment C-Digiy model 3600 (LI-COR) for 7 minutes for imaging.

Detection of IFNγ in the supernatant of L. lactis cultures. To detect the protein from the supernatant of L. lactis cultures, the supernatant was collected after centrifuging the bacterial culture, then it was precipitated with 6 volumes of acetone and stored at −20° C. overnight. Afterwards, it was centrifuged at 6,000 RPM for 10 min at 4° C., then the supernatant was discarded and the precipitate was washed 2 times with double distilled water, finally, the pellet was resuspended in 50 uL of protein lading buffer. To detect the protein the Western Blot protocol described above was used.

IFNγ mRNA quantification in L. lactis cultures. To correlate the induction of protein with IFNγ messenger RNA levels generated by L. lactis (FIG. 4), culture and induction conditions were replicated. After nisin induction for 2 hours, the bacterial culture was centrifuged at 6,000 RPM at 4° C. for 10 minutes, the supernatant was discarded and the bacteria was lysed in 1 mL of TRIzol to extract total RNA according to the manufacturer's recommendations. Afterwards, RNA was treated with DNase I (Promega®) to remove traces of contaminant plasmidial DNA, then this was used to quantify the number of IFNγ coding mRNA copies by qRT-PCR. The reaction mix was: 2 uL of total RNA (100 ng), 5 uL od 2× SensiMix SYBR No-ROX One-Step Kit, 0.5 uL of IFNγ L. lactis Fw primer, 0.5 uL of IFNγ L. lactis Rv primer (10 mM) (Table 2) and 2 uL of nuclease free water.

Biological activity of IFNγ produced by L. lactis. To determine if the produced protein was biologically active, cytoplasmatic extracts of the bacteria were incubated with SHK-1 cells, cells derived from Salmo salar (Table 1) and then some transcripts involved in the response to IFNγ were quantified. Briefly, different proportions between L. lactis and L. lactis-IFNγ cytoplasmatic extracts were mixed with L-15 medium and incubated for 8 hours at 16° C. with SHK-1 cells to determine the contribution of the recombinant protein amount from the total protein content by the bacteria. Afterwards, total RNA from salmon cells was extracted using the E.Z.N.A Total RNA kit (OMEGA biotek) and treated with DNase I (Promega®). Treated RNA was used for synthesis of cDNA with Oligo(dT) with the following reaction mix: 11 uL of treated RNA, 0.5 uL of Oligo(dt) (10 mM), 1 uL of dNTPs (10 mM each), 0.2 uL of M-MLV (Promega®), 7 uL of nuclease free water. The obtained cDNA was diluted 1:2 and used for relative quantification of transcripts related to the immune response by qPCR with the following reaction mix: 2 uL of cDNA, 5 uL of 2× SensiMix SYBR No-ROX Kit, 0.25 uL of Fw (10 mM), 0.25 uL of Rv (10 mM) and 2 uL of nuclease free water (Table 2).

TABLE 1

(FIG. 5) Amount of total protein used in assays to determine the contribution of IFNγ to the immune response of SHK-1 cells. Samples with 20 ug of total protein amount were obtained by mixingsonicated lysate of IFNγ expressing L. lactis (L. L IFNγ) and lysate of L. lactis that does not express it (L. L empty) in different proportions. Starting from the sample containing 20 ug of total protein all working dilutions were prepared.

| L. L IFNγ (ug) | L. L empty (ug) | Final protein content (ug) |
|---|---|---|
| 0.0 | 20.0 | 20 |
| 2.0 | 18.0 | 20 |
| 6.0 | 14.0 | 20 |
| 10.0 | 10.0 | 20 |
| 14.0 | 6.0 | 20 |
| 20.0 | 0.0 | 20 |

TABLE 2

Nucleotide sequence of primers used for quantification of immune response genes and studied pathogens.

| Gene | Primer | 5' → 3' |
|---|---|---|
| IFNγ salmon | FW | CCG TAC ACC GAT TGA GGA CT |
| | RV | GCG GCA TTA CTC CAT CCT AA |
| IL-1b salmon | FW | CCC CAT TGA GAC TAA AGC CA |
| | RV | GCA ACC TCC TCT AGG TGC AG |
| TGF-β salmon | FW | AGC TCT CGG AAG AAA CGA CA |
| | RV | AGT AGC CAG TGG GTT CAT GG |
| gamma IP10 salmon | FW | GTG TCT GAA TCC AGA GGC TCC A |
| | RV | TCT CAT GGT GCT CTC TGT TCC A |
| IFNγ L. lactis-IFNγ | FW | CAC ATT TGC AAA ATC TTT GGG CT |
| | RV | CAA TCG TTG TGC TTG TCG TCT |
| IL-6 salmon | FW | CCT TGC GGA ACC AAC AGT TTG |
| | RV | CCT CAG CAA CCT TCA TCT GGT C |
| IL-12 salmon | FW | TGA CGC TTT TTC TCA CCG GTT GT |
| | RV | ACG CTT TGC AGC ATG AGC TTG A |
| eF1α salmon | FW | GGG TGA GTT TGA GGC TGG TA |
| | RV | TTC TGG ATC TCC TCA AAC CG |

TABLE 2-continued

Nucleotide sequence of primers used for quantification of immune
response genes and studied pathogens.

| Gene | Primer | 5' → 3' |
|---|---|---|
| RpoS *F. psychrophilum* | FW | GAA GAT GGA GAA GGT AAT TTA GTT GAT ATT |
| | RV | CAA ATA ACA TCT CCT TTT TCT ACA ACT TGA |
| STAT1 | FW | GAC CAG CGA ACC CAA GAA CCT GAA |
| | RV | CAC AAA GCC CAG GAT GCA ACC AT |
| rDNA 16S *P. salmonis* | FW | AGG GAG ACT GCC GGT GAT A |
| | RV | ACT ACG AGG CGC TTT CTC A |

Result Description pNZ8149 has a food grade selection marker that allows lactose metabolism (LacF), it has a constitutive promoter P1 and a nisin inducible promoter, *L. lactis*' natural secretion signal Usp45, *Salmo salar* IFNγ codifying gene and a histidine tag. RepA and RepC are genes that allow the plasmid's replication (FIG. 1). When transforming NZ3900 bacteria, which presents a chromomsomal deletion of the lactose ORF, the bacteria can use this carbon sourse and keep the plasmid. The constitutive promoter P1 allows the expression of IFNγ, this induction can be proportionaly increased with the amount of nisin added to culture media due to the pNisA promoter (FIG. 2). The protein can be easily detected from the cytoplasmatic fraction by Western Blot, however the amount of secreted protein is in a much lower proportion (FIG. 3). This increase in the amount of protein detected by Wester Blot can be seen when quantifying the number of transcripts of IFNγ mRNA by qRT-PCR (FIG. 4).

When using the cytoplasmitic extract of sonicated bacteria on salmon SHK-1 cell line, normalizing the amount of total protein (Table 1) it is possible to detect the induction of transcripts such as STAT1, gIP10 and IL-1b, suggesting that the protein is functional in vitro because the first two are involved in the signalling cascade initiated by IFNγ and the third is involved in the natural proimmflamatory response following IFNg. (FIG. 5). However, when quantifying IL-6, a pleitropic cytokine related to an induced innate immune response, it increases proportionally with the amount of recombinant protein present in culture, surprisingly suggesting that IFNγ would be inducing its expression.

Example 2: Effects of Administering IFNγ Producing *L. lactis* Bacteria

Figure 6:
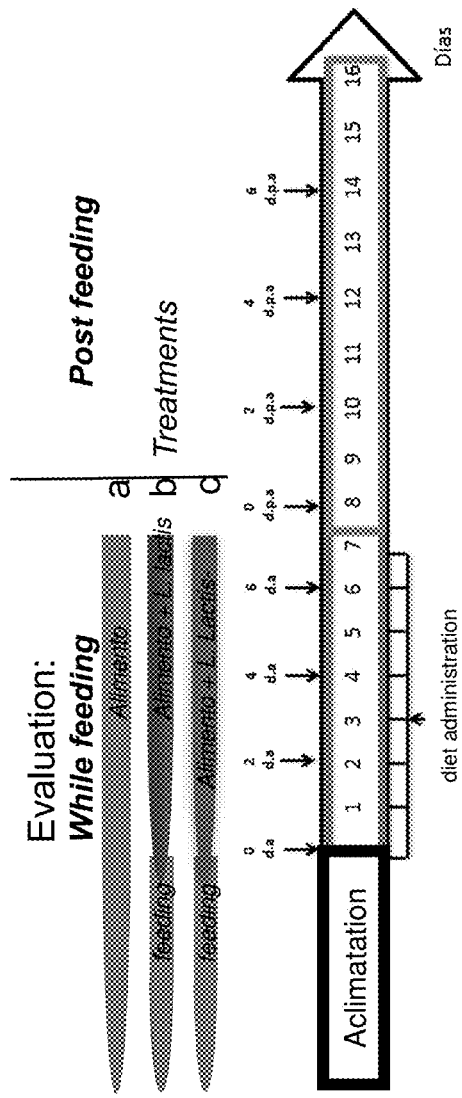
FIG. 6. Feeding outline with IFNγ producing *L. lactis* in in vivo experiment with rainbow trout. Fish were first acclimated for 7 days prior to treatment; then, a 7 day feeding period began with a) commercial feed, b) *L. lactis* transformed with an empty plasmid, c) *L. lactis*-IFNγ. At day 0 (before treatment), 2, 4 and 6 3 fish were sampled. Afterwards, treatment was suspended and all fish were given commercial feed. Finally, 3 fish were sampled from each group at days 1, 3, 5 and 7 days after probiotic feed. (d.p.f) during probiotic feeding and (a.p.f) after probiotic feeding.
Figure 7B:
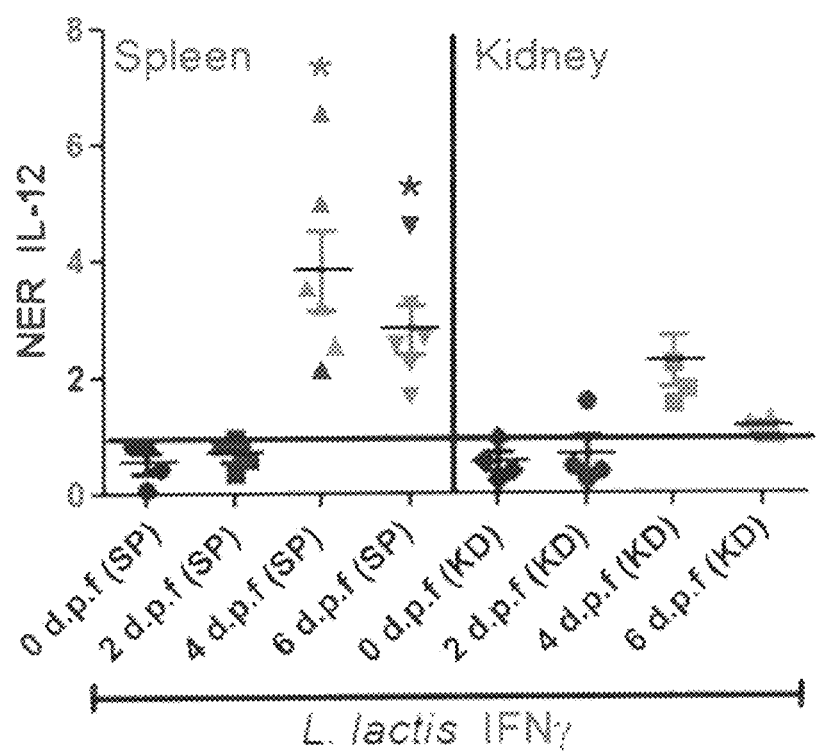
FIG. 7*b* shows RT-qPCR quantification of mRNA related to immune response of interferon gamma (IFNγ) during feeding of *Lactococcus lactis*-IFNγ to rainbow trout. Relative quantification was performed to different genes that responded to IFNγ. Spleen (SP) and kidney (KD) simples were studied at day 0, 2, 4 and 6 during probiotic feeding (d.p.f) Relative expression of IL-12 was performed normalizing against eF1a. One-tailed Mann-Whitney analysis was performed, and significance was determined by t-student ($p<0.05$) comparing expression levels to those observed on day 0 before probiotic feeding. NER: Normalized relative expression. Finally, 3 fish were sampled from each group at all timepoints and all assays were performed in technical duplicates.
Figure 7C:
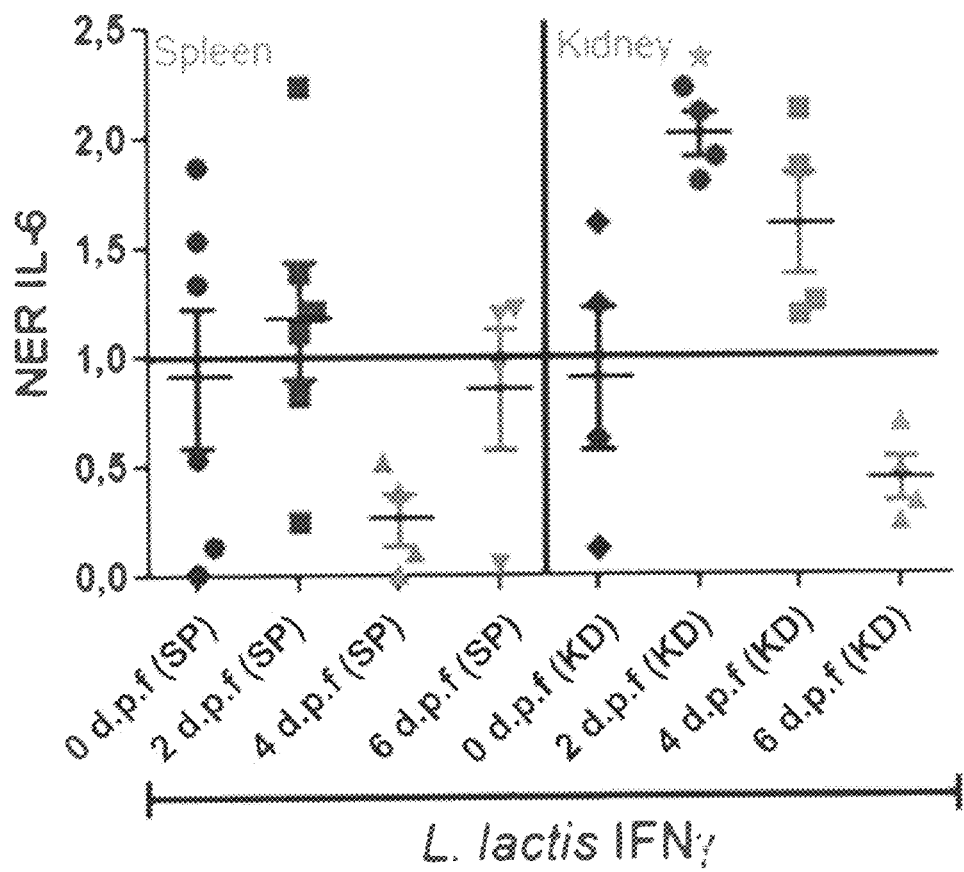
FIG. 7*c* shows RT-qPCR quantification of mRNA related to immune response of interferon gamma (IFNγ) during feeding of *Lactococcus lactis*-IFNγ to rainbow trout. Relative quantification was performed to different genes that responded to IFNγ. Spleen (SP) and kidney (KD) simples were studied at day 0, 2, 4 and 6 during probiotic feeding (d.p.f) Relative expression of IL-6 was performed normalizing against eF1a. One-tailed Mann-Whitney analysis was performed, and significance was determined by t-student ($p<0.05$) comparing expression levels to those observed on day 0 before probiotic feeding. NER: Normalized relative expression. Finally, 3 fish were sampled from each group at all timepoints and all assays were performed in technical duplicates.
Figure 7D:
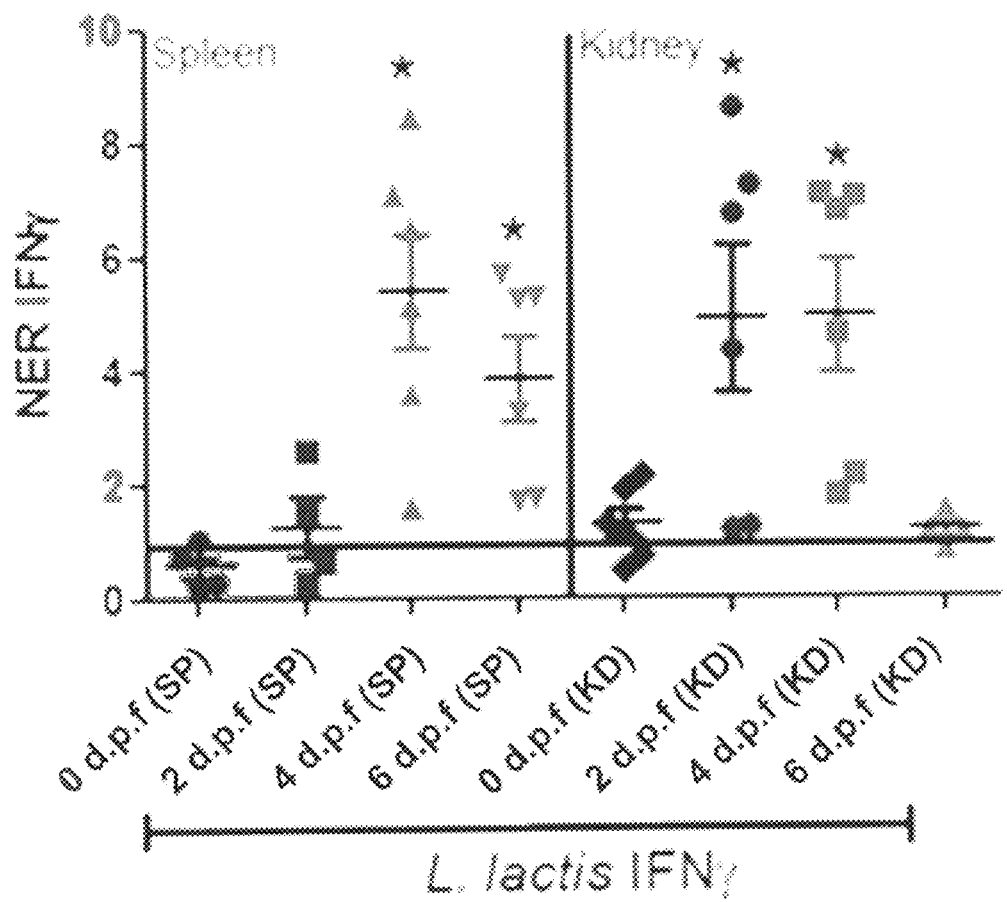
FIG. 7*d* shows RT-qPCR quantification of mRNA related to immune response of interferon gamma (IFNγ) during feeding of *Lactococcus lactis*-IFNγ to rainbow trout. Relative quantification was performed to different genes that responded to IFNγ. Spleen (SP) and kidney (KD) simples were studied at day 0, 2, 4 and 6 during probiotic feeding (d.p.f) Relative expression of IFNγ was performed normalizing against eF1a. One-tailed Mann-Whitney analysis was performed, and significance was determined by t-student (p<0.05) comparing expression levels to those observed on day 0 before probiotic feeding. NER: Normalized relative expression. Finally, 3 fish were sampled from each group at all timepoints and all assays were performed in technical duplicates.
Figure 7E:
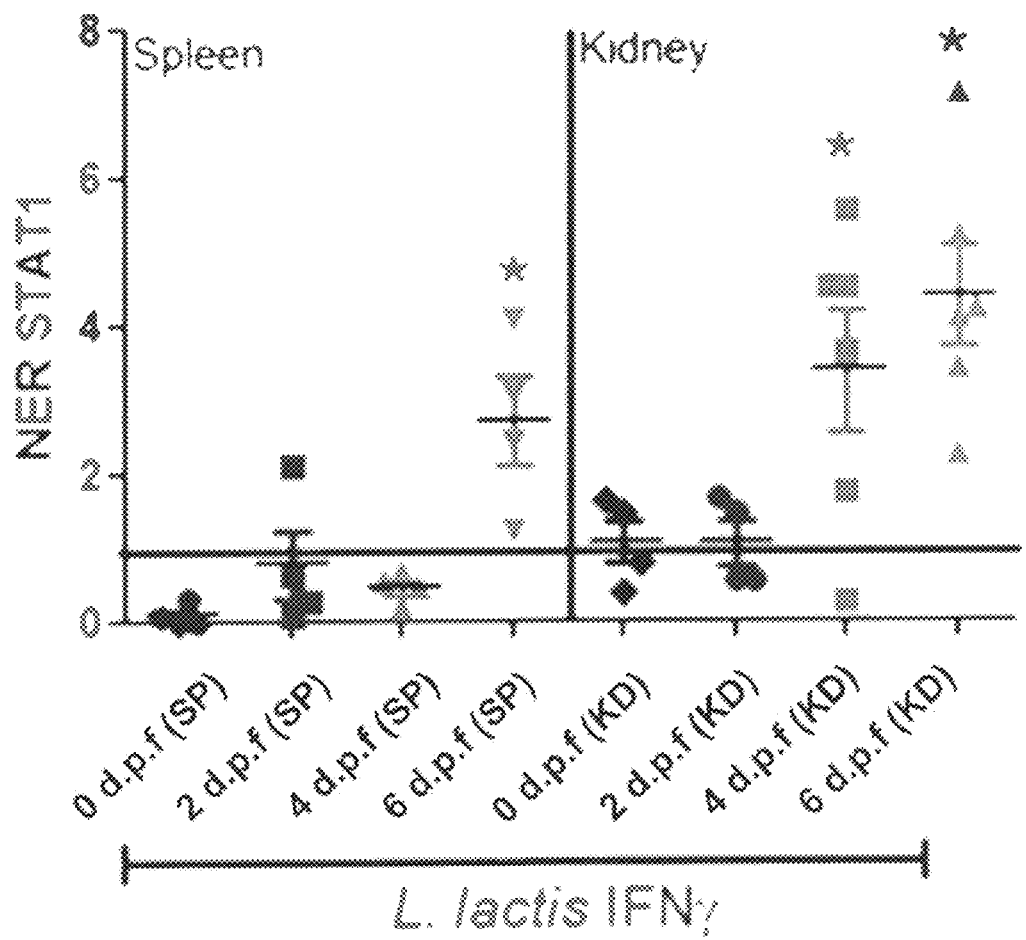
FIG. 7e shows RT-qPCR quantification of mRNA related to immune response of interferon gamma (IFNγ) during feeding of *Lactococcus lactis*-IFNγ to rainbow trout. Relative quantification was performed to different genes that responded to IFNγ. Spleen (SP) and kidney (KD) simples were studied at day 0, 2, 4 and 6 during probiotic feeding (d.p.f) Relative expression of STAT1 was performed normalizing against eF1a. One-tailed Mann-Whitney analysis was performed, and significance was determined by t-student (p<0.05) comparing expression levels to those observed on day 0 before probiotic feeding. NER: Normalized relative expression. Finally, 3 fish were sampled from each group at all timepoints and all assays were performed in technical duplicates.
Figure 7F:
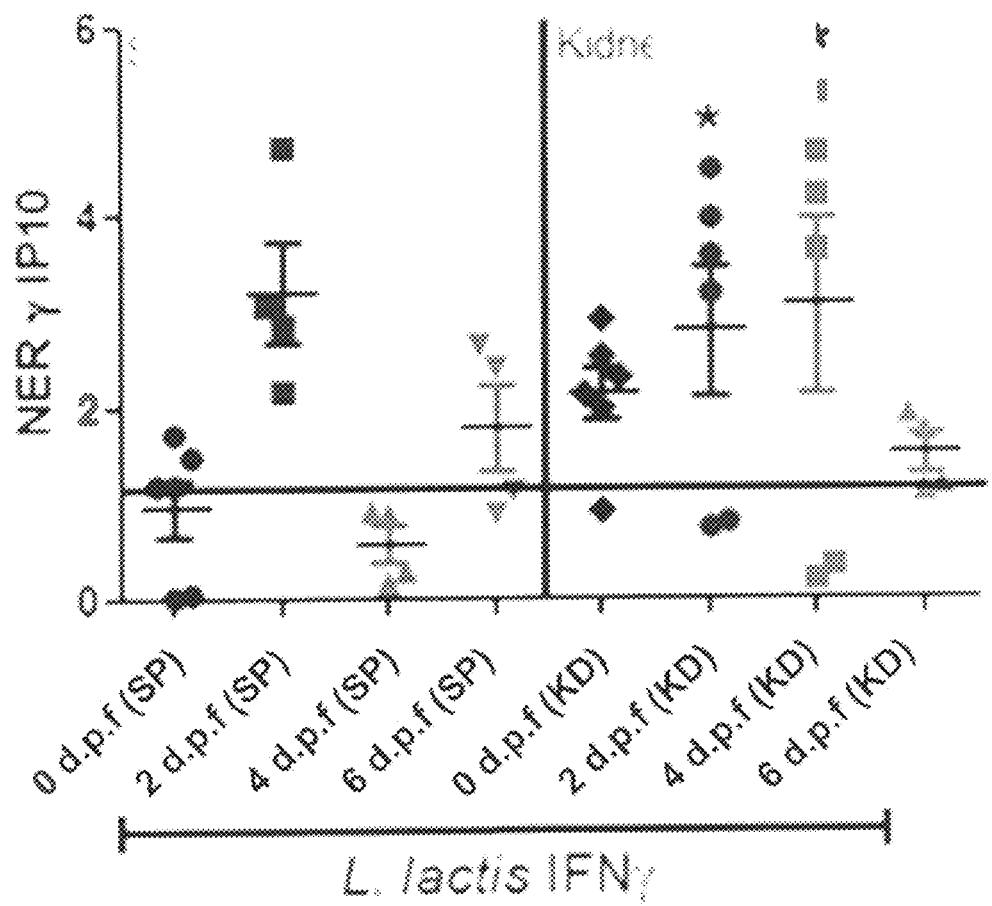
FIG. 7f shows RT-qPCR quantification of mRNA related to immune response of interferon gamma (IFNγ) during feeding of *Lactococcus lactis*-IFNγ to rainbow trout. Relative quantification was performed to different genes that responded to IFNγ. Spleen (SP) and kidney (KD) simples were studied at day 0, 2, 4 and 6 during probiotic feeding (d.p.f) Relative expression of gIP10 was performed normalizing against eF1a. One-tailed Mann-Whitney analysis was performed, and significance was determined by t-student (p<0.05) comparing expression levels to those observed on day 0 before probiotic feeding. NER: Normalized relative expression. Finally, 3 fish were sampled from each group at all timepoints and all assays were performed in technical duplicates.

To assess the immunoestimulating effect of IFNγ producing *L. lactis* in an in vivo model an assay was performed with rainbow trouts (average weight: 20-25 g) were the effect of the probiotic was evaluated through the course of the experiment during and after feeding it as it is described in FIG. 6.

The approach consisted in acclimating the fish for 7 days, then feeding them for 7 days with a) *L. lactis*-IFNγ, b) *L. lactis* with an empty vector and c) commercial feed. At day 0 (before treatment), 2 and 6 and 3 fish were sampled. Afterwards, treatment was suspended and all fish were given commercial feed. Then, 3 fish were sampled from each group at days 1, 3, 5 and 7 days after probiotic feed. While sampling, during probiotic feed (d.p.f) and after probiotic feed (a.p.f), 100 uL of blood was extracted from 3 fish, which were then sacrificed prior to spleen and kidney extraction. Blood was used to quantify lysozyme enzymatic activity in serum by means of *Micrococcus luteus* suspensions. The assay consisted in measuring the decrease of absorbance at 450 nm in 180 uL of a *M. luteus* stock incubated with 20 uL of serum, using as a positive control 200-400 units of lysozyme/mL.

The following formula was used to calculate the amount of lysozyme:

$$\text{units/ml enzyme} = \frac{(\Delta A_{450}/\text{min Sample} - \Delta A_{450}/\text{min Blanc})}{(0.001)(0.02)}$$

To determine if stimulation of the immune response at a transcript level occurs, total RNA from spleen and kidney was extracted with TRIzol following the manufacturers recommendation. Then, cytokines IL-1β, IL-6, IL-12, TGF-β, IFNγ, gamma IP10 and STAT1 were quantified by relative quantification. Treated RNA with DNase I was used as template for cDNA synthesis with Oligo(dT) following this reaction mixture: 11 uL od treated RNA, 0.5 uL of Oligo(dt) (10 mM), 1 uL of dNTP (10 mM each), 0.5 uL of M-MLV (Promega®), 7 uL of nuclease free water. The obtained cDNA was diluted 1:2 and used as template for relative quantification of the transcripts related to the immune response by qPCR with the following reaction mix: 2 uL of cDNA, 5 uL of 2× SensiMix SYBR No-ROX Kit, 0.25 uL of Fw (10 mM), 0.25 uL of Rv (10 mM) and 2 uL of nuclease free water (Table 2).

To assess if the observed immunostimulation is able to create protection against pathogens relevant to salmon farming, a challenge in rainbow trouts (average weight: 15-20 g) was set up using *F. psychrophilum* ($1 \times 10^8$ bacteria/fish) as model. Fish were acclimated for 7 days prior to treatment; then, a 7 day special feeding period began and 5 days later the challenge was performed. Afterwards, mortality was registered during the following 18 days to asses immune response and bacterial load.

In this assay the following treatments were studied: a) Fish fed for 7 days with *L. lactis*-IFNγ($1 \times 10^7$ bacteria/fish) and then infected, b) Fish fed for 7 days with *L. lactis* with an empty vector ($1 \times 10^7$ bacteria/fish) and then infected and c) Fish fed for 7 days with commercial feed and then infected. Mortality was registered for 17 days after infection, time during which spleen of dying fish was extracted and from fish that survived the experiment for bacterial load quantification To determine if higher doses or a prolonged diet could increase survival, a second challenge in rainbow trout (average weight: 30-40 g) was performed with *F. psychrophilum* ($1\times10^8$ bacteria/fish). In this assay, fish were acclimated for 7 days, then special feeding began for 7 days and 5 days afterwards the challenge was performed. The following conditions were studied: a) Fish fed for 7 days with a doses 3 times higher than the original of *L. lactis*-IFNγ ($3\times10^7$ bacteria/fish) and then infected, b) Fish fed for 13 days with *L. lactis*-IFNγ ($1\times10^7$ bacteria/fish) and then infected, c) Fish fed for 7 days with *L. lactis*-IFNγ ($1\times10^7$ bacteria/fish) and then infected, d) Fish fed for 7 days with *L. lactis* with and empty plasmid ($1\times10^7$ bacteria/fish) and then infected and e) Fish fed for 7 days with a commercial feed and then infected. To determine if probiotic administration changes the physical condition, length and weight of surviving fish was recorded.

To assess the protective effect of *L. lactis*-IFNγ on *Salmo salar*, the intracellular bacteria *Pisirickettsia salmonis* was used as a model ($1\times10^7$ bacteria/fish). Fish were first acclimated for 7 days and then the following treatments began: a) Fish fed for 7 days *L. lactis*-IFNγ ($1\times10^7$ bacteria/fish) and then infected, b) Fish fed for 14 days *L. lactis*-IFNγ ($1\times10^7$ bacteria/fish) and then infected, c) Fish fed for 7 days with *L. lactis* with and empty plasmid ($1\times10^7$ bacteria/fish) and then infected and d) Fish fed for 7 days with commercial feed and then infected. Mortality was recorded for 23 days after infection.

Bacterial Load: Bacterial load of infected fish with *P. salmonis* or *F. psycrophillum* was determined by absolute qPCR using total DNA extracted from the immunological organs spleen and kidney. From these organs, total DNA was extracted with the Wizzart Genomic DNA Kit (Promega®). Purified DNA was quantified by absorbance at 260 nm. 50 ng of total DNA were used for the qPCR reaction. To detect *P. psycrophillum* the primers rpoS-F (5' GAA GAT GGA GAA GGT AAT TTA GTT GAT 3') and rpoS-R (5' CAA ATA ACA TCT CCT TTT TCT ACA ACT 3') were used, which amplify a 200 bp fragment. To detect *P. salmonis* the primers 16SPS-F (5' AGG GAG ACT GCC GGT GAT A 3') and 16SPS-R (5' ACT ACG AGG CGC TTT CTC A 3') were used. Each amplification product showed only one denaturation peak indicating a specific amplification product. For each one of the amplicons a calibration curve was constructed with increasing concentrations of the PCR product previously cloned on pGEM-T. Through this method the number of bacteria was calculated, assuming that there is only one copy of the gene in each bacterium chromosome.

Result Description

Figure 8:
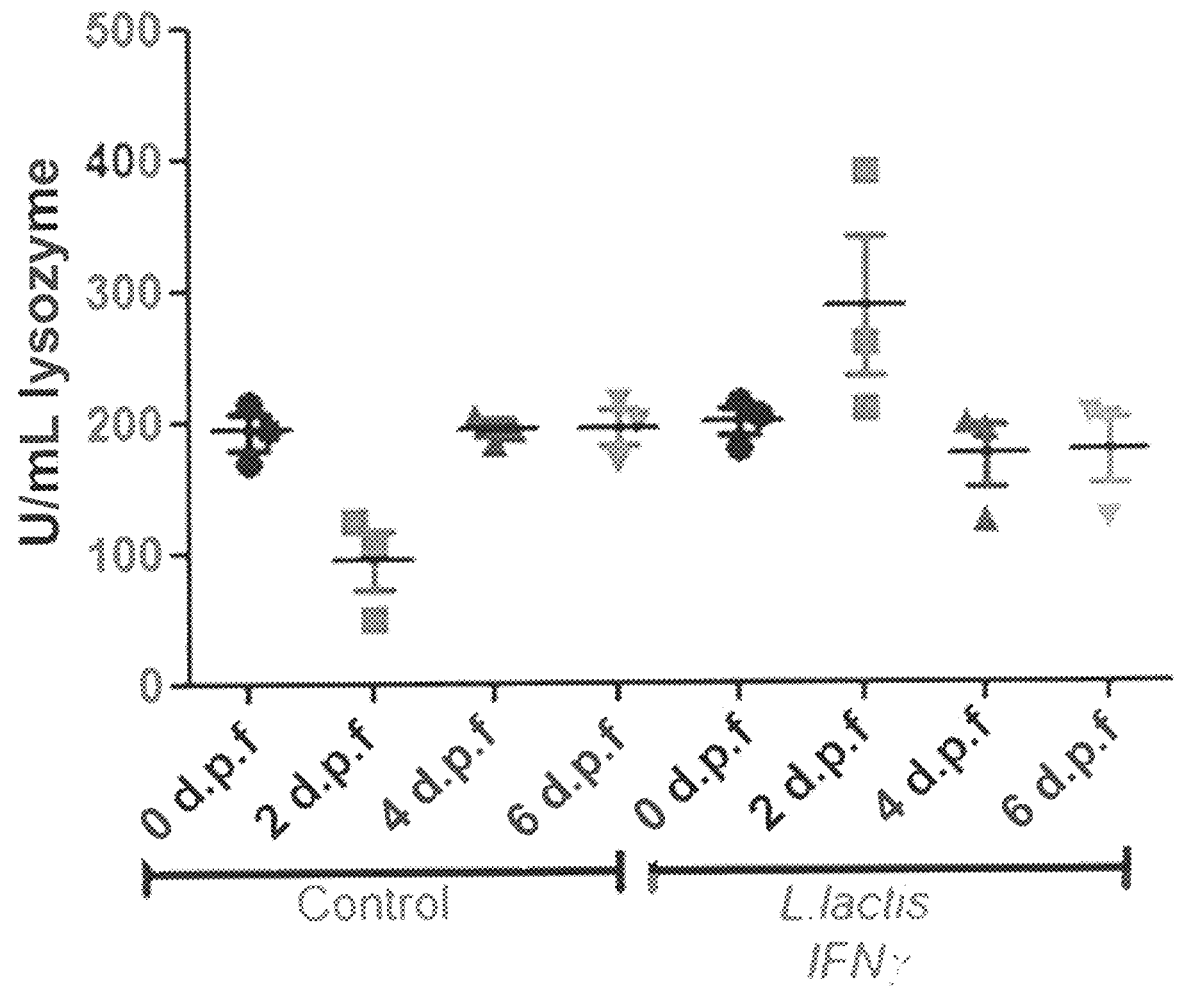
FIG. 8. Lysozyme quantification in rainbow trout serum during treatment with *L. lactis*-IFNγ. Trouts were fed during 7 days with feed supplemented with *L. lactis*-IFNγ or commercial feed (control). Blood samples were taken at the beginning of the experiment (day 0 d.p.f) and days 2, 4 and 6 during probiotic feed. Serum was obtained from blood samples by centrifuging at 4,500 RPM for 15 minutes at 4° C. The amount of lysozyme was quantified using the *Micrococcus lutheus* assay observing reduction of optic density, absorbance was measured in a Tecan Pro200 Nanoquant. Finally, 3 fish were sampled from each group at each timepoint. (d.p.f) during probiotic feeding.
Figure 9A:
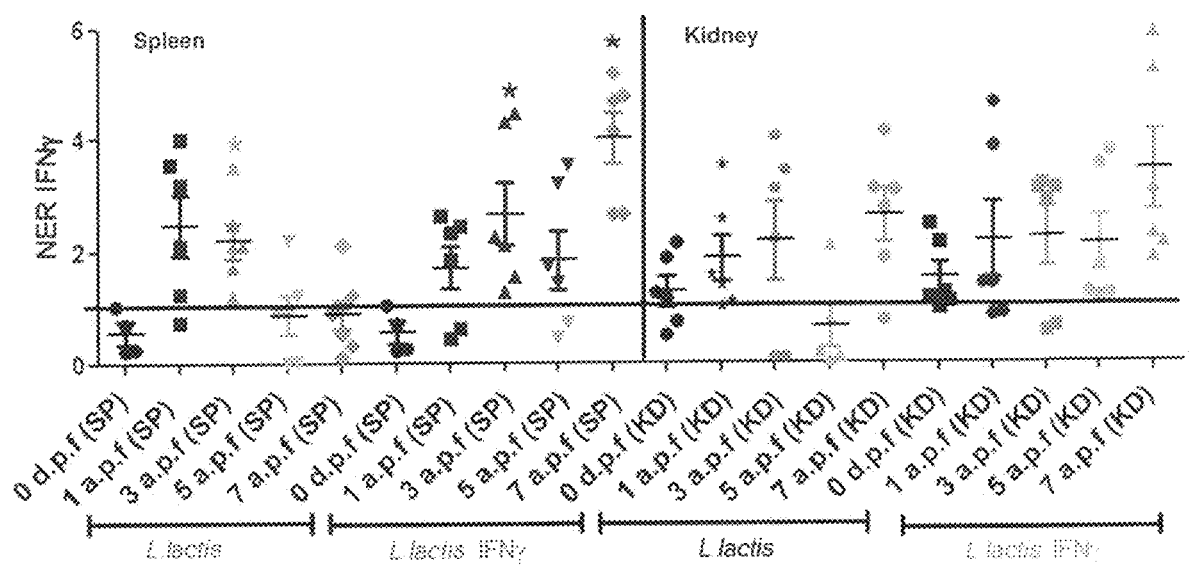
FIG. 9a shows RT-qPCR quantification of mRNA related to immune response of interferon gamma (IFNγ) after feeding of *Lactococcus lactis*-IFNγ to rainbow trout. Relative quantification was performed to different genes that responded to IFNγ. Spleen (SP) and kidney (KD) simples were studied at day 0, 1, 3 and 7 after probiotic feeding (a.p.f). Relative expression of IFNγ (A) was performed using eF1a as normalizing gene and compared results to expression levels on day 0 d.p.f, before probiotic feeding. One-tailed Mann-Whitney analysis was performed, and significance was determined by t-student (p<0.05) comparing expression levels to those observed on day 0 before probiotic feeding. NER: Normalized relative expression. Finally, 3 fish were sampled from each group and all assays were performed in technical duplicates.
Figure 9B:
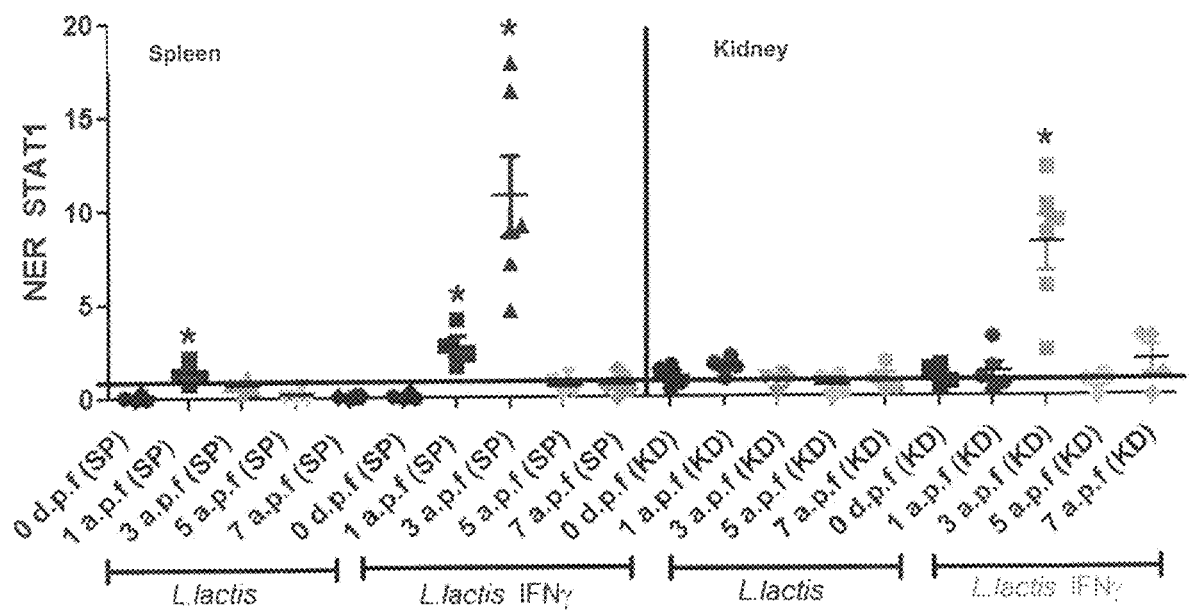
FIG. 9b shows RT-qPCR quantification of mRNA related to immune response of interferon gamma (IFNγ) after feeding of *Lactococcus lactis*-IFNγ to rainbow trout. Relative quantification was performed to different genes that responded to IFNγ. Spleen (SP) and kidney (KD) simples were studied at day 0, 1, 3 and 7 after probiotic feeding (a.p.f). Relative expression of STAT1(B) was performed using eF1a as normalizing gene and compared results to expression levels on day 0 d.p.f, before probiotic feeding. One-tailed Mann-Whitney analysis was performed, and significance was determined by t-student (p<0.05) comparing expression levels to those observed on day 0 before probiotic feeding. NER: Normalized relative expression. Finally, 3 fish were sampled from each group and all assays were performed in technical duplicates.
Figure 9C:
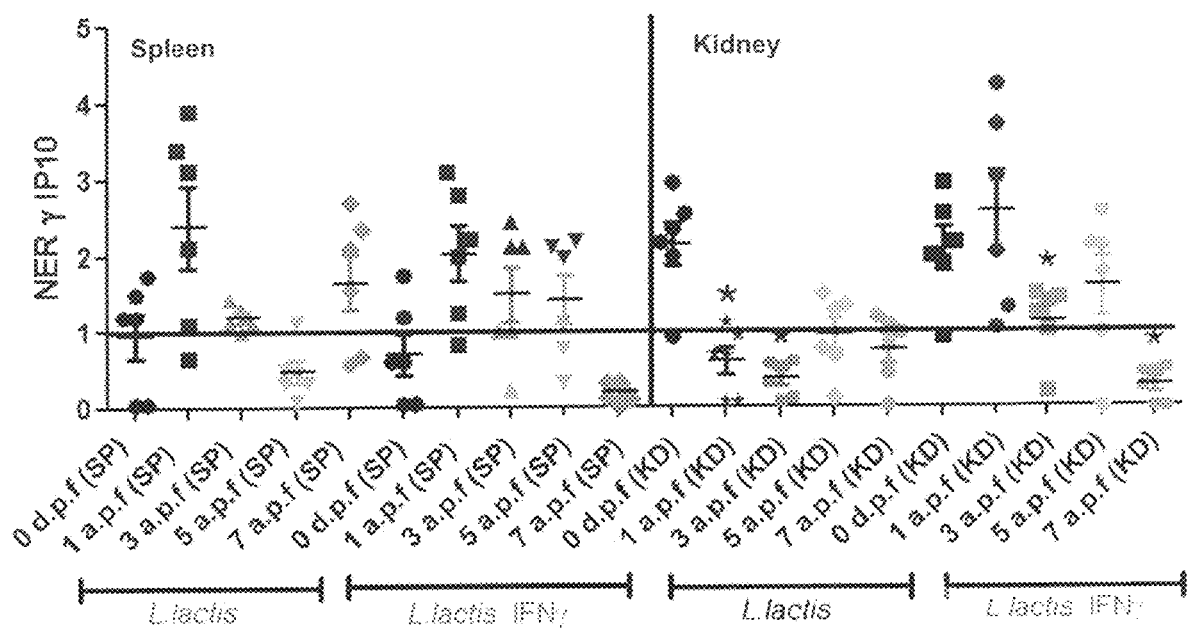
FIG. 9c shows RT-qPCR quantification of mRNA related to immune response of interferon gamma (IFNγ) after feeding of *Lactococcus lactis*-IFNγ to rainbow trout. Relative quantification was performed to different genes that responded to IFNγ. Spleen (SP) and kidney (KD) simples were studied at day 0, 1, 3 and 7 after probiotic feeding (a.p.f). Relative expression of gIP10 (C) was performed using eF1a as normalizing gene and compared results to expression levels on day 0 d.p.f, before probiotic feeding. One-tailed Mann-Whitney analysis was performed, and significance was determined by t-student (p<0.05) comparing expression levels to those observed on day 0 before probiotic feeding. NER: Normalized relative expression. Finally, 3 fish were sampled from each group and all assays were performed in technical duplicates.
Figure 9D:
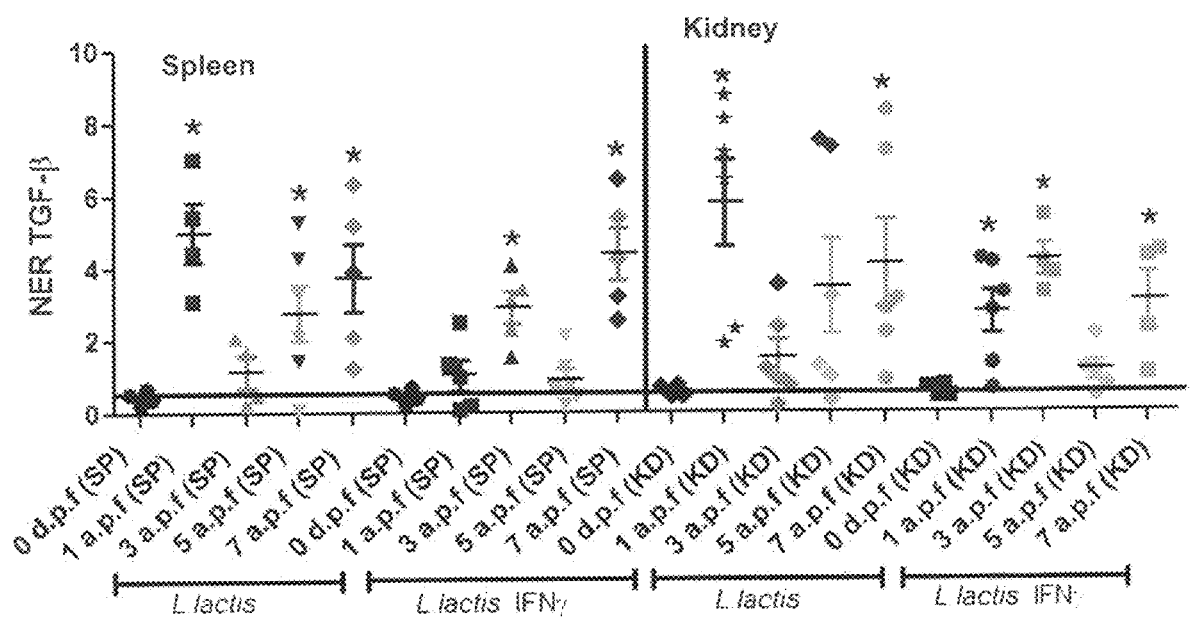
FIG. 9d shows RT-qPCR quantification of mRNA related to immune response of interferon gamma (IFNγ) after feeding of *Lactococcus lactis*-IFNγ to rainbow trout. Relative quantification was performed to different genes that responded to IFNγ. Spleen (SP) and kidney (KD) simples were studied at day 0, 1, 3 and 7 after probiotic feeding (a.p.f). Relative expression of TGF-β (D) was performed using eF1a as normalizing gene and compared results to expression levels on day 0 d.p.f, before probiotic feeding. One-tailed Mann-Whitney analysis was performed, and significance was determined by t-student (p<0.05) comparing expression levels to those observed on day 0 before probiotic feeding. NER: Normalized relative expression. Finally, 3 fish were sampled from each group and all assays were performed in technical duplicates.
Figure 9E:
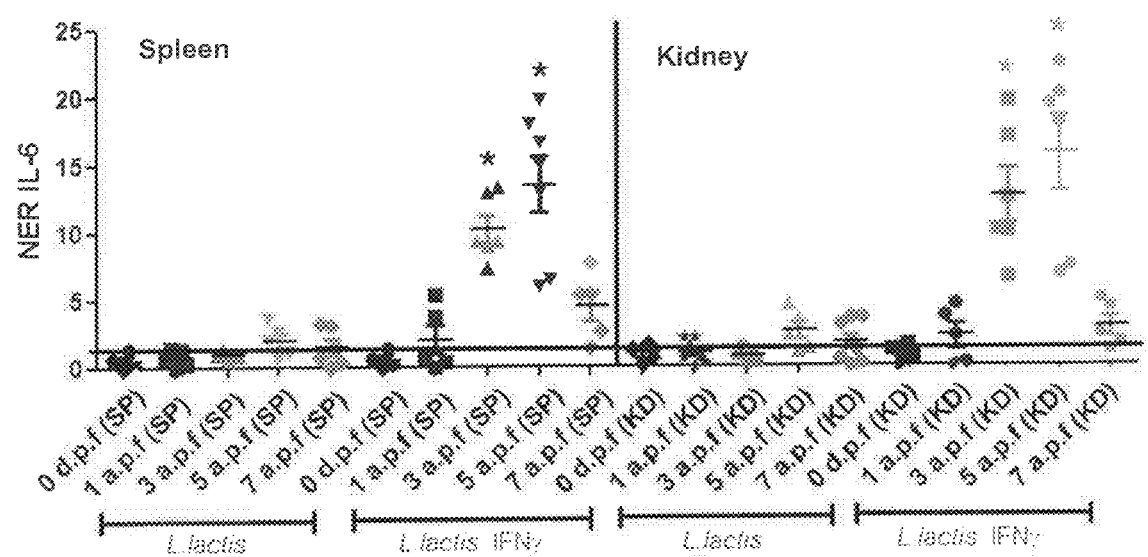
FIG. 9e shows RT-qPCR quantification of mRNA related to immune response of interferon gamma (IFNγ) after feeding of *Lactococcus lactis*-IFNγ to rainbow trout. Relative quantification was performed to different genes that responded to IFNγ. Spleen (SP) and kidney (KD) simples were studied at day 0, 1, 3 and 7 after probiotic feeding (a.p.f). Relative expression of IL-6 (E) was performed using eF1a as normalizing gene and compared results to expression levels on day 0 d.p.f, before probiotic feeding. One-tailed Mann-Whitney analysis was performed, and significance was determined by t-student (p<0.05) comparing expression levels to those observed on day 0 before probiotic feeding. NER: Normalized relative expression. Finally, 3 fish were sampled from each group and all assays were performed in technical duplicates.
Figure 10:
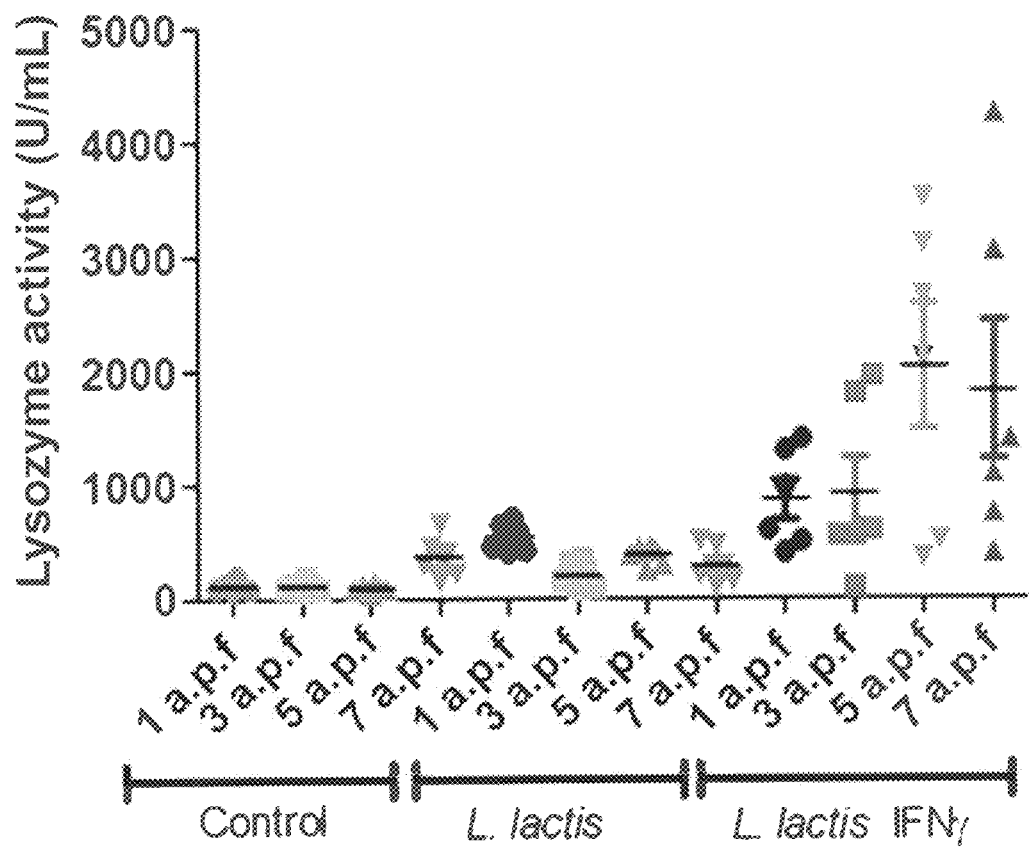
FIG. 10. Lysozyme quantification in rainbow trout serum after treatment with *L. lactis*-IFNγ. Trouts were fed during 7 days with feed supplemented with probiotic or commercial feed (control) and then fed with commercial feed. Blood samples were taken at days 1, 3, 5 and 7 days after probiotic feeding. Serum was obtained from blood samples by centrifuging at 4,500 RPM for 15 minutes at 4° C. The amount of lysozyme was quantified using the *Micrococcus lutheus* assay observing reduction of optic density, absorbance was measured in a Tecan Pro200 Nanoquant. Three groups of fish were sampled, the first group was given commercial feed throughout the experiment (control), the second group fish was fed with *L. lactis* NZ3900 (empty plasmid) and the third group fish was given IFNγ expressing *L. lactis* (*L. lactis* IFNγ). Finally, 3 fish were sampled from each group at each timepoint and all assays were performed in technical duplicates. (d.p.f) during probiotic feeding

To asses the in vivo effect, transformed bacteria was administrated with feed to healthy rainbow trout specimens, then these were analyzed during and after feeding. Two paramenters were studied from spleen and kidney: a) transcripts related to immune respone of IFNg from spleen and kidney during probiotic feeding (FIG. 7) and after probiotic feeding (FIG. 9A to E) and b) lysozyme enzymatic activity from serun during (FIG. 8) and after probiotic feeding (FIG. 10). When observing transcript changes it is possible to see an increase of IL-12, STAT1 and gamma IP10, the first is involved in cellular response triggered by IFNg increase and the second two are related to the downstream response of IFNg. When studying the effect of the probiotic after feeding, no significant increase can be observed in the transcripts related to type II IFN, but the anti-inflammatory cytokine TGF-b is stimulated and IL-6 increases considerably from the fifth day after feeding, effect that correlates to what is observed in cell culture. When quantifying lysozyme's enzymatic activity no increases are seen during feeding, however, a strong increase in seen from the fifth day after feeding as observed for IL-6 by qPCR, which suggested that the cytokine could be involved in the levels of lysozyme in serum.

Figure 11A:
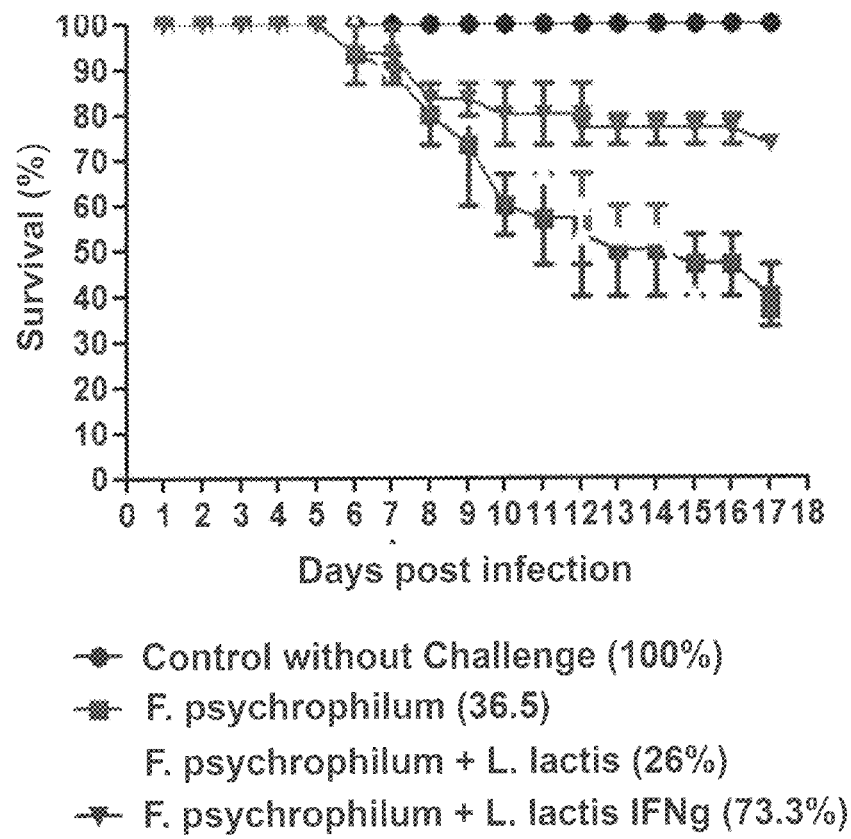
FIG. 11a shows mortality caused by *F. psychrophilum* in infected rainbow trout fed with *L. lactis* IFNγ. Six fish tanks (AQ1-AQ6) were used, each with 15 fish of approximately 25 g. Fish were challenged with *F. psychrophilum* by intraperitoneal injection of 100 uL ($1.25 \times 10^9$ UFC) of inoculum and mortality was observed for 17 days (12° C.). (A) Survival percentage of each studied group. No-challenge Control: fish injected with TYES medium. Flavo: fish infected with *F. psychrophilum*. Flavo+*L. lactis*: fish fed for 7 days with *L. lactis* and then challenged with *F. psychrophilum*. Flavo+*L. lactis* IFNγ: fish fed for 7 days with *L. lactis* expressing IFNγ and then challenged with *F. psychrophilum*. 100% corresponds to 15 fish per tank.
Figure 11B:
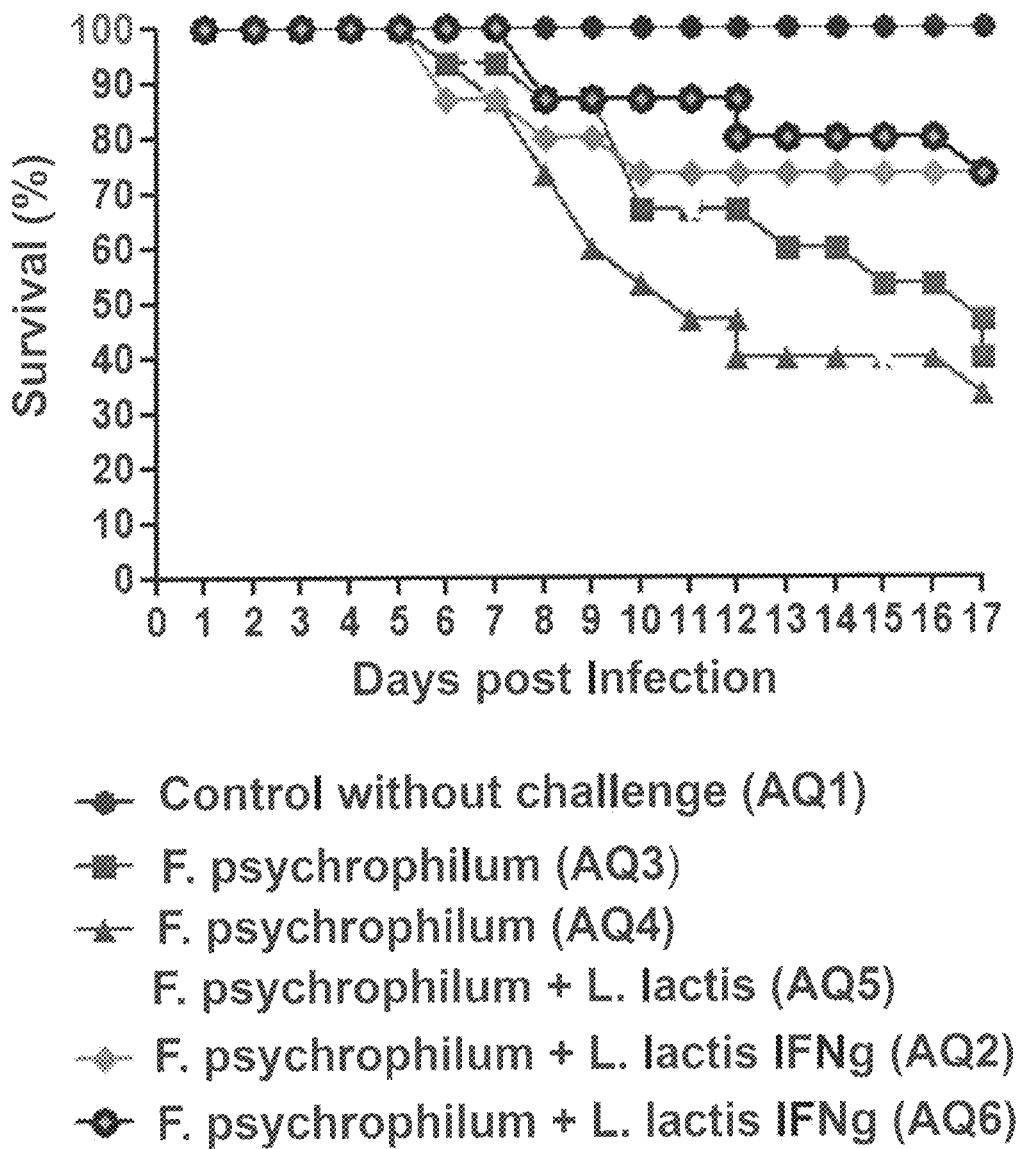
FIG. 11b shows mortality caused by *F. psychrophilum* in infected rainbow trout fed with *L. lactis* IFNγ. Six fish tanks (AQ1-AQ6) were used, each with 15 fish of approximately 25 g. Fish were challenged with *F. psychrophilum* by intraperitoneal injection of 100 uL ($1.25 \times 10^9$ UFC) of inoculum and mortality was observed for 17 days (12° C.). (B) Survival percentage in each fish tank. No-challenge Control: fish injected with TYES medium. Flavo: fish infected with *F. psychrophilum*. Flavo+*L. lactis*: fish fed for 7 days with *L. lactis* and then challenged with *F. psychrophilum*. Flavo+*L. lactis* IFNγ: fish fed for 7 days with *L. lactis* expressing IFNγ and then challenged with *F. psychrophilum*. 100% corresponds to 15 fish per tank.
Figure 12:
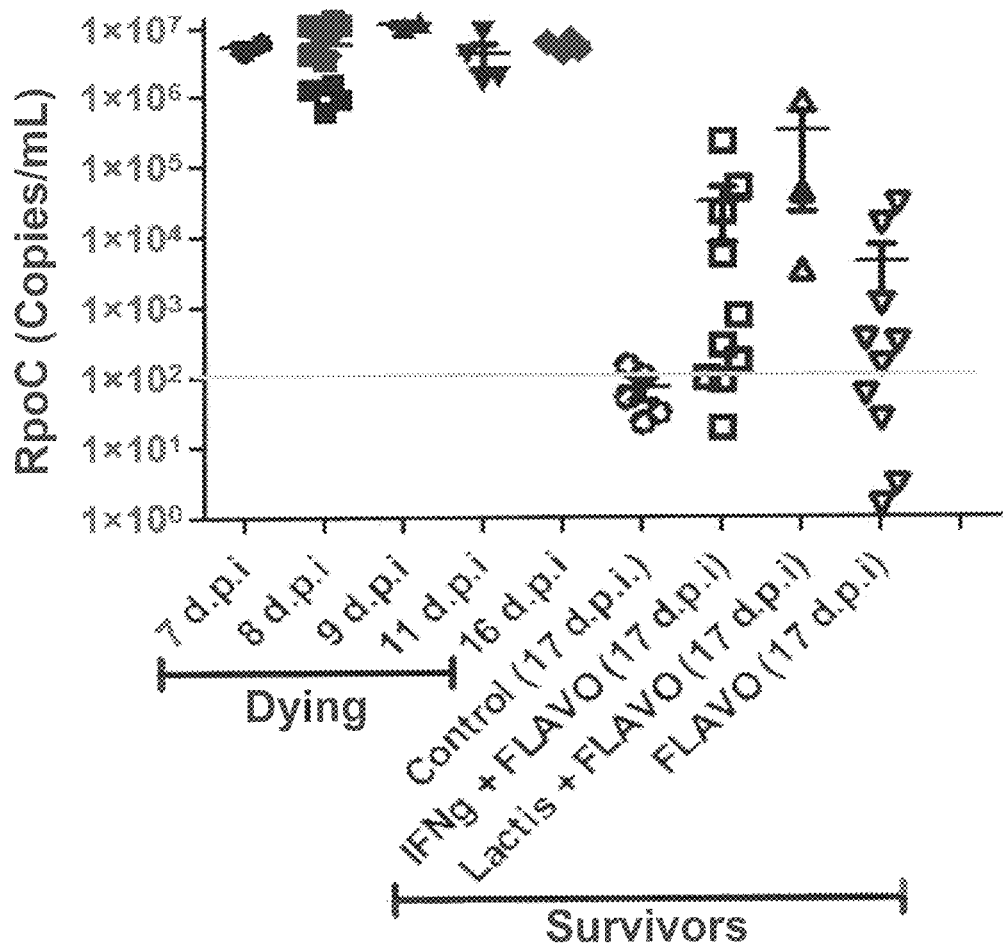
FIG. 12. Number of copies of *F. psychrophilum* RpoS/mL from infected rainbow trout spleen. Trouts were fed with feed supplemented with either commercial feed, *L. lactis*-IFNγ(IFNγ) or *L. lactis* (Lactis). Fish were challenged with *F. psychrophilum* (Flavo) by intraperitoneal injection. Studied groups were FLAVO, IFNγ+FLAVO and Lactis+FLAVO respectively, as negative control (control) fish were fed commercial feed and injected with physiological serum. Using qPCR RpoC was quantified to determine bacterial load in dying and surviving fish after the challenge. Dying fish appeared 7 days after infection and surviving fished were those that did not show signs of dying at day 17 after infection. Bacterial load values below the red line are considered noise associated to the technique.

Given that estimulation of type II IFN related genes was observed, the protective effect of the probiotic was assessed, for this an experiment was set up where rainbow trout were challenged with *Flavobacterium psychrophillum* (FIG. 11). Fish fed with *L. lactis*-IFNγ (Treatment a)) presented a survival percentage higher than 70%, effect that was not seen in fish fed with *L. lactis* with an empty vector which only reached 35% survival (Treatment b). Fish that did not receive probiotic treatment presented lower survival (25%) (Treatment c)). When comparing bacterial load of fish that died during the experiment and surviving fish, a decline of at least 2 orders of magnitude in the number of bacterial RpoS gene copies can be observed (FIG. 12). Therefore, the heterologous protein produced by *L. lactis* would be protecting fish from infection of *F. psychrophilum*.

Figure 13:
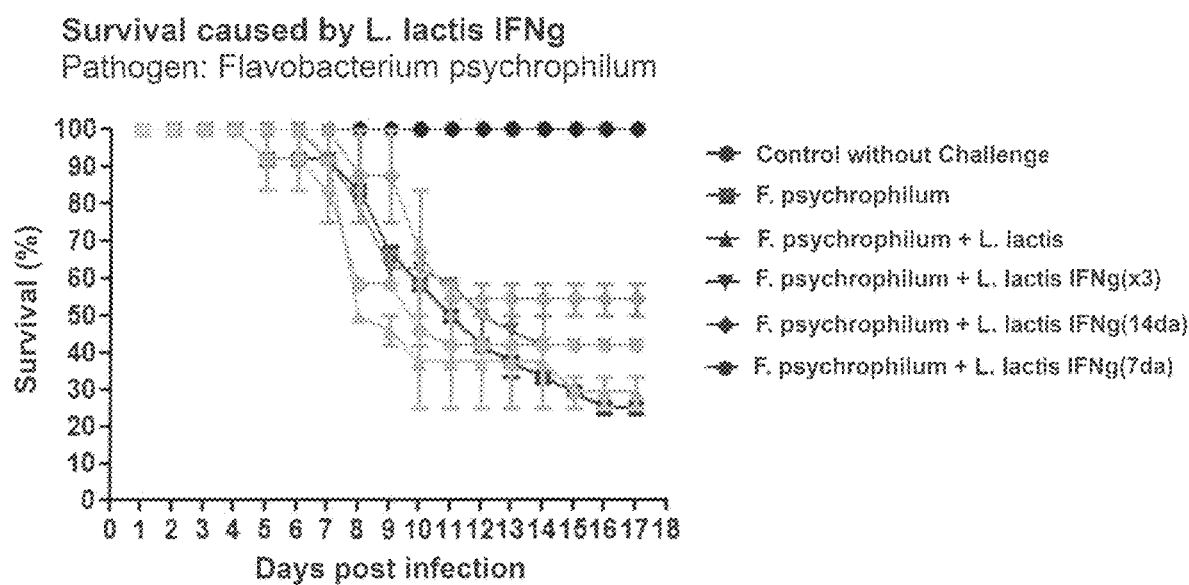
FIG. 13. Mortality caused by *F. psychrophilum* in infected rainbow trout fed with *L. lactis* IFNγ. Twelve fish tanks (AQ1-AQ12) were used, each with 12 fish of approximately 30 g. Fish were challenged with *F. psychrophilum* by intraperitoneal injection of 100 uL ($1.25 \times 10^9$ UFC) of inoculum and mortality was observed for 17 days (12° C.). Control: fish injected with TYES medium. Flavo: fish infected with *F. psychrophilum*. Flavo+*L. lactis*: fish fed for 7 days with $1 \times 10^7$ UFC of *L. lactis* per fish and then challenged with *F. psychrophilum*. Flavo+*L. lactis* IFNγ (7da): fish fed for 7 days with $1 \times 10^7$ UFC of *L. lactis* expressing IFNg and then challenged with *F. psychrophilum*. Flavo+*L. lactis* IFNγ (×3): fish fed for 7 days with $3 \times 10^7$ UFC of *L. lactis* expressing IFNγ and then challenged with *F. psychrophilum*. Flavo+*L. lactis* IFNγ (14da): fish fed for 14 days with $1 \times 10^7$ UFC of *L. lactis* expressing IFNγ and then challenged with *F. psychrophilum*.
Figure 14A:
FIG. 14a shows weight of surviving rainbow trouts in each experimental condition at the end of experiment shown in FIG. 13. Control: fish injected with TYES medium. Flavo: fish infected with *F. psychrophilum*. Flavo+*L. lactis*: fish fed for 7 days with $1 \times 10^7$ UFC of *L. lactis* per fish and then challenged with *F. psychrophilum*. Flavo+*L. lactis* IFNγ (7da): fish fed for 7 days with $1 \times 10^7$ UFC of *L. lactis* expressing IFNγ and then challenged with *F. psychrophilum*. Flavo+*L. lactis* IFNg (×3): fish fed for 7 days with $3 \times 10^7$ UFC of *L. lactis* expressing IFNγ and then challenged with *F. psychrophilum*. Flavo+*L. lactis* IFNγ(14da): fish fed for 14 days with $1 \times 10^7$ UFC of *L. lactis* expressing IFNγ and then challenged with *F. psychrophilum*. Duplicates are shown as independent experiments.
Figure 14B:
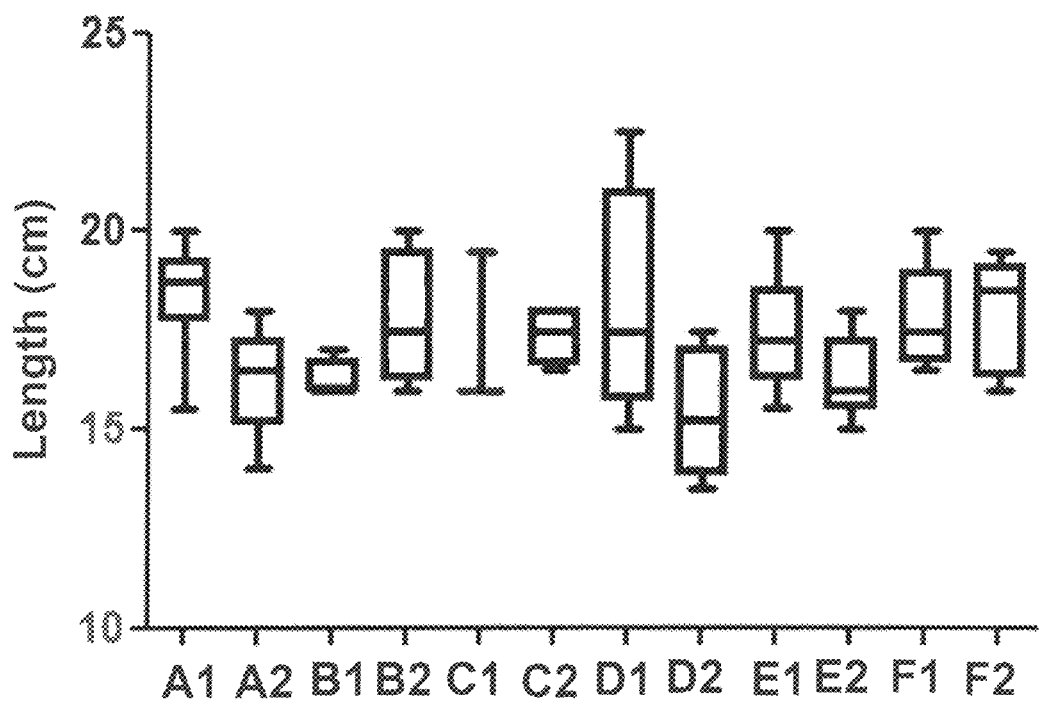
FIG. 14b shows length of surviving rainbow trouts in each experimental condition at the end of experiment shown in FIG. 13. Control: fish injected with TYES medium. Flavo: fish infected with *F. psychrophilum*. Flavo+*L. lactis*: fish fed for 7 days with $1 \times 10^7$ UFC of *L. lactis* per fish and then challenged with *F. psychrophilum*. Flavo+*L. lactis* IFNγ (7da): fish fed for 7 days with $1 \times 10^7$ UFC of *L. lactis* expressing IFNγ and then challenged with *F. psychrophilum*. Flavo+*L. lactis* IFNg (×3): fish fed for 7 days with $3 \times 10^7$ UFC of *L. lactis* expressing IFNγ and then challenged with *F. psychrophilum*. Flavo+*L. lactis* IFNγ (14da): fish fed for 14 days with $1 \times 10^7$ UFC of *L. lactis* expressing IFNγ and then challenged with *F. psychrophilum*. Duplicates are shown as independent experiments.

When administrating *L. lactis*-IFNγ for a longer period of time (13 days instead of 7), it was observed higher survival (54%) than in fish fed for 7 days (42%), the same effect was seen in fish fed with a dosage 3 times higher than the original one (42%), which indicates that prolonging feeding gives a better result (FIG. 13). Fish fed only with *L. lactis* (Treatment d)) presented a lower survival percentage (29%), very close to the 25% observed in fish fed with commercial feed (Treatment e)), behaviour also observed in the previous assay. The lower protection across different treatments could be due to the higher weight of fish (30-40 g versus 15-20 g), suggesting that the probiotic presents better properties in early stages of rainbow trout. When assessing weight or length of the surviving fish at the end of the experiment no significant differences were found (FIG. 14), suggestion that the probiotic does not alter the physical state of fish.

Figure 15A:
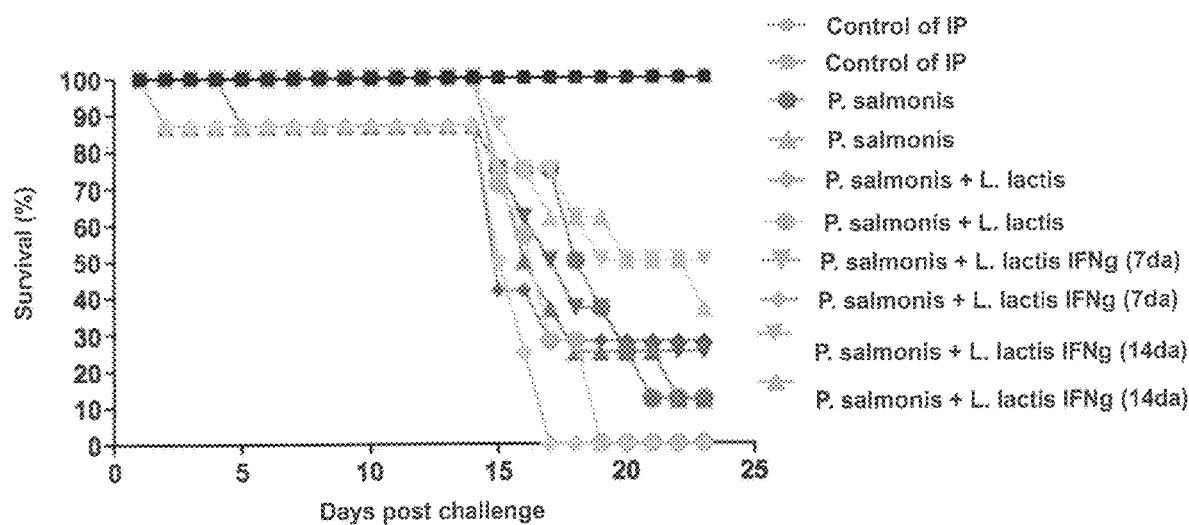
FIG. 15a shows mortality caused by *Piscirickettsia salmonis* in infected *Salmo salar* fed with *L. lactis* IFNγ. Five experimental conditions, each with a biological duplicate, were studied in 10 fish tanks, each with 8 fish of approximately 45 g. Fish were challenged with *P. salmonis* by intraperitoneal injection of 100 uL ($1 \times 10^7$ live bacteria/mL) of inoculum. (A) Survival percentage in each fish tank. Injection control: fish injected with L15 medium. Challenge control: fish infected by intraperitoneal injection of 100 uL ($1 \times 10^7$ live bacteria/mL) *P. salmonis*. *L. lactis*+SRS: fish infected by intraperitoneal injection of 100 uL ($1 \times 10^7$ live bacteria/mL) *P. salmonis*, fed for 7 days *L. lactis* and given a 3-day booster. *L. lactis* IFNγ (IFNg) (7da)+SRS: fish infected by intraperitoneal injection of 100 uL ($1 \times 10^7$ live bacteria/mL) *P. salmonis*, fed for 7 days *L. lactis* IFNγ and given a 3-day booster. *L. lactis* IFNγ (IFNγ) (14da)+SRS: fish infected by intraperitoneal injection of 100 uL ($1 \times 10^7$ live bacteria/mL) *P. salmonis* and fed for 14 days *L. lactis* IFNγ. Results are shown in duplicates.
Figure 15B:
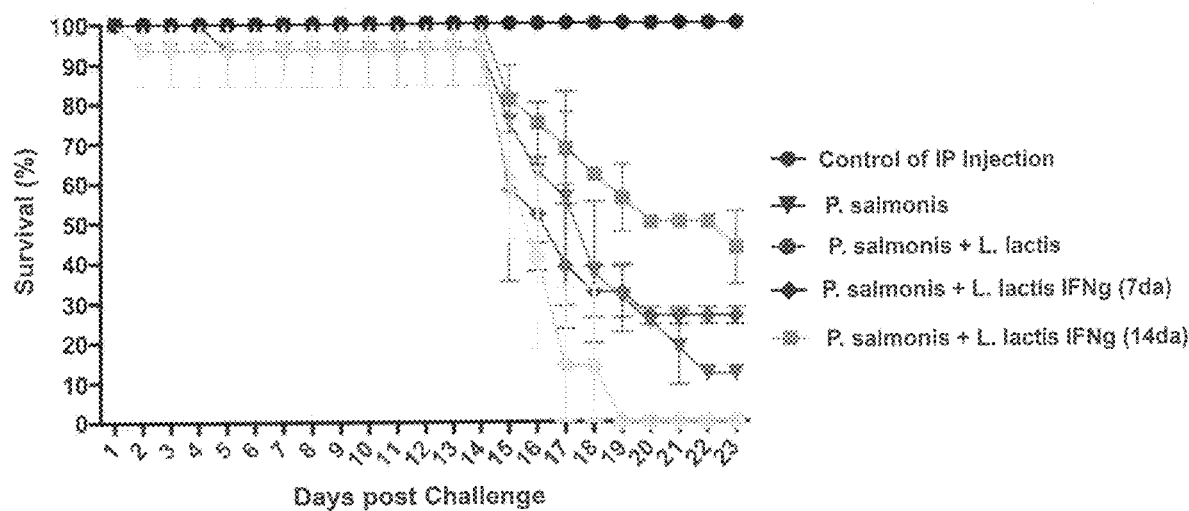
FIG. 15b shows mortality caused by *Piscirickettsia salmonis* in infected *Salmo salar* fed with *L. lactis* IFNγ. Five experimental conditions, each with a biological duplicate, were studied in 10 fish tanks, each with 8 fish of approximately 45 g. Fish were challenged with *P. salmonis* by intraperitoneal injection of 100 uL ($1 \times 10^7$ live bacteria/mL) of inoculum. (B) Survival percentage per studied condition. Injection control: fish injected with L15 medium. Challenge control: fish infected by intraperitoneal injection of 100 uL ($1 \times 10^7$ live bacteria/mL) *P. salmonis*. *L. lactis*+SRS: fish infected by intraperitoneal injection of 100 uL ($1 \times 10^7$ live bacteria/mL) *P. salmonis*, fed for 7 days *L. lactis* and given a 3-day booster. *L. lactis* IFNγ (IFNg) (7da)+SRS: fish infected by intraperitoneal injection of 100 uL ($1 \times 10^7$ live bacteria/mL) *P. salmonis*, fed for 7 days *L. lactis* IFNγ and given a 3-day booster. *L. lactis* IFNγ (IFNγ) (14da)+SRS: fish infected by intraperitoneal injection of 100 uL ($1 \times 10^7$ live bacteria/mL) *P. salmonis* and fed for 14 days *L. lactis* IFNγ. Results are shown in duplicates.

The potential use of the probiotic in *Salmo salar* challenged with *Pisciricketssia salmonis* was studied, fish fed with *L. lactis*-IFNg for 7 days (Treatment a: 28% survival) present a slight increase in protection compared to fish treated with the probiotic for 14 days (treatment b: 25% survival) suggesting that the protective effect against *P. salmonis* is given when feeding fish for 7 days and then it is maintained constant. On the other hand, fish fed with *L. lactis* with an empty vector (treatment c: 0% survival) presented total mortality, however, fish fed with *L. lactis* with the plasmid without insert/commercial feed showed significant disparity in their mortality (Treatment d: 12% and 50% each replica). Therefore, *L. lactis*-IFNγ can contribute to the survival of fish infected with *P. salmonis* (FIG. 15).

Figure 16:
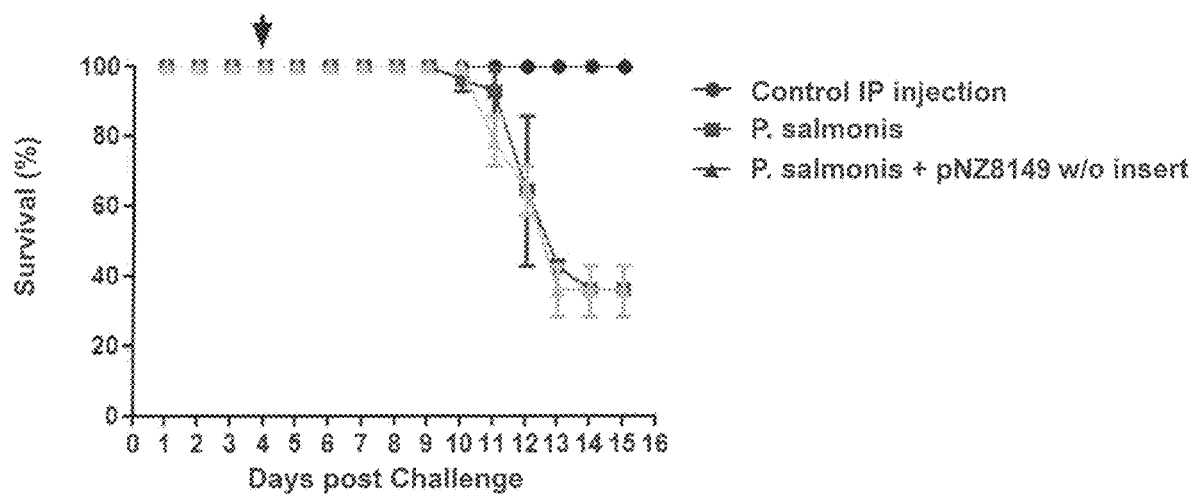
FIG. 16. Mortality caused by *Piscirickettsia salmonis* in infected *Salmo salar* fed with *L. lactis* transformed with an empty plasmid. Three experimental conditions, each with a biological duplicate were studied in 6 fish tanks, each with 7 fish of approximately 50 g. Fish were fed for 7 days and then challenged with *P. salmonis* by intraperitoneal injection. Vehicle control: fish injected with L15 medium. *P. salmonis*: fish injected with *P. salmonis* ($1\times10^7$ live bacteria/fish) of inoculum. *P. salmonis*+pNZ8149 w/o insert: *Salmo salar* fed with feed supplemented with *L. lactis* transformed with the vector pNZ8149 without *S. salar*'s IFNγ gene and challenged with *P. salmonis* ($1\times10^7$ live bacteria/fish). Graphs show average survival percentage in each condition.

To determine if *L. lactis* pNZ8149 without insert has an effect on survival of fish challenged with *P. salmonis*, the experiment was repeated with *Salmo salar* specimens (average weight: 50 g) infected and fed with probiotic (FIG. 16), observing that their registered mortality was the same than for infected fish fed with commercial feed, which indicates that the bacteria per se does not confer protection.

Sequences

<110> Consorcio Tecnológico de Sociedad Acuícola S.A. y Universidad de Santiago

<120> *Lactococcus Lactis* bacteria transformed, RGM2416, producing Salmo salar interferon gamma (IFNg), feed an composition that comprises it, to immunostimulate aquatic species and prevent infection of *F. psychrophilium*, *P. salmonis* or both and methos to obtain it.

<160> 5

<210> 1

<211> 779

<212> ADN

<400> 1

| | | | | | |
|---|---|---|---|---|---|
| ccatggtata | gatctaatta | atctataaac | catatccctc | tttggaatca | aaatttatta | 60 |
| tctactcctt | tgtagatatg | ttataataca | agtatcaatg | atctgggaga | ccacaacggt | 120 |
| ttcccactag | aaataatttt | gtttaacttt | agaaaggaga | tatacgcatg | aaaaaaaaga | 180 |
| ttatctcagc | tattttaatg | tctacagtga | actttctgc | tgcagccccg | ttgtcaggtg | 240 |
| tttacgctgc | tcaatataca | tcaattaata | tgaaatcaaa | tattgataaa | cttaaagtac | 300 |
| attataaaat | tagtaaagat | caattgttta | atggaaaacc | agttttttcct | aaagatacat | 360 |
| ttgaagattc | agaacgtaga | gtttggatgt | ctgttgtatt | agatgtatat | cgttcaattt | 420 |
| ttaatcaaat | gcttaatcaa | acaggtgatc | aagaagtacg | tgaaagatta | gatcaagtta | 480 |
| aaggaaaagt | acaagaaact | caaaaacatt | attttcttaa | acgaattcca | gaattgagaa | 540 |
| cacatttgca | aaatctttgg | gctattgaaa | ctagtaatac | aactgttcaa | ggaaaagcat | 600 |
| tgtcagaatt | tattactatt | tatgaaaaag | cttctaaatt | agcacttaaa | attcatttaa | 660 |
| agaaagataa | tcgacgtaaa | agacgacaag | cacaacgatt | gaaaagtagt | attatgggag | 720 | gtggacatca tcatcatcat cattaaaaaa aagtcttaaa ataataaaaa tagtctaga

<210> 2

<211> 161

<212> ADN

<400> 2

| | | | | | |
|---|---|---|---|---|---|
| tatagatcta | attaatctat | aaaccatatc | cctctttgga | atcaaaattt | attatctact | 60 |
| cctttgtaga | tatgttataa | tacaagtatc | aatgatctgg | gagaccacaa | cggtttccca | 120 | ctagaaataa ttttgtttaa ctttagaaag gagatatacg c

<210> 3

<211> 81

<212> ADN

<400> 3

| | | | | | |
|---|---|---|---|---|---|
| atgaaaaaaa | agattatctc | agctatttta | atgtctacag | tgatactttc | tgctgcagcc | 60 | ccgttgtcag gtgtttacgc t

<210> 4

<211> 468

<212> ADN

<400> 4

| | | | | | |
|---|---|---|---|---|---|
| gctcaatata | catcaattaa | tatgaaatca | aatattgata | aacttaaagt | acattataaa | 60 |
| attagtaaag | atcaattgtt | taatggaaaa | ccagttttttc | ctaaagatac | atttgaagat | 120 |

-continued

```
tcagaacgta gagtttggat gtctgttgta ttagatgtat atcgttcaat ttttaatcaa    180
atgcttaatc aaacaggtga tcaagaagta cgtgaaagat tagatcaagt taaaggaaaa    240
gtacaagaaa ctcaaaaaca ttattttctt aaacgaattc cagaattgag aacacatttg    300
caaaatcttt gggctattga aactagtaat acaactgttc aaggaaaagc attgtcagaa    360
tttattacta tttatgaaaa agcttctaaa ttagcactta aaattcattt aagaaagat     420 aatcgacgta aaagacgaca agcacaacga ttgaaaagta gtattatg

<210>    5
<211>    24
<212>    ADN
<400>    5 ggaggtggac atcatcatca tcat
```

---

SEQUENCE LISTING

```
Sequence total quantity: 27
SEQ ID NO: 1              moltype = DNA   length = 779
FEATURE                   Location/Qualifiers
misc_feature              1..779
                          note = gene encoding to Salmo Salar immunostimulating
                           protein
source                    1..779
                          mol_type = other DNA
                          organism = synthetic construct
SEQUENCE: 1
ccatggtata gatctaatta atctataaac catatccctc tttggaatca aaatttatta   60
tctactcctt tgtagatatg ttataataca agtatcaatg atctgggaga ccacaacggt   120
ttcccactag aaataatttt gtttaacttt agaaaggaga tatacgcatg aaaaaaaaga   180
ttatctcagc tattttaatg tctacagtga tactttctgc tgcagccccg ttgtcaggtg   240
tttacgctgc tcaatataca tcaattaata tgaaatcaaa tattgataaa cttaaagtac   300
attataaaat tagtaaagat caattgttta atggaaaacc agttttttcct aaagatacat   360
ttgaagattc agaacgtaga gtttggatgt ctgttgtatt agatgtatat cgttcaattt   420
ttaatcaaat gcttaatcaa acaggtgatc aagaagtacg tgaaagatta gatcaagtta   480
aaggaaaagt acaagaaact caaaaacatt attttcttaa acgaattcca gaattgagaa   540
cacatttgca aaatctttgg gctattgaaa ctagtaatac aactgttcaa ggaaaagcat   600
tgtcagaatt tattactatt tatgaaaaag cttctaaatt agcacttaaa attcatttaa   660
agaaagataa tcgacgtaaa agacgacaag cacaacgatt gaaaagtagt attatgggag   720
gtggacatca tcatcatcat cattaaaaaa aagtcttaaa ataataaaaa tagtctaga    779

SEQ ID NO: 2              moltype = DNA   length = 161
FEATURE                   Location/Qualifiers
misc_feature              1..161
                          note = Primer expressing IFNg
source                    1..161
                          mol_type = other DNA
                          organism = synthetic construct
SEQUENCE: 2
tatagatcta attaatctat aaaccatatc cctctttgga atcaaaattt attatctact   60
cctttgtaga tatgttataa tacaagtatc aatgatctgg gagaccacaa cggttttccca  120
ctagaaataa ttttgtttaa ctttagaaag gagatatacg c                       161

SEQ ID NO: 3              moltype = DNA   length = 81
FEATURE                   Location/Qualifiers
misc_feature              1..81
                          note = secreting IFNg
source                    1..81
                          mol_type = other DNA
                          organism = synthetic construct
SEQUENCE: 3
atgaaaaaaa agattatctc agctatttta atgtctacag tgatactttc tgctgcagcc   60
ccgttgtcag gtgtttacgc t                                             81

SEQ ID NO: 4              moltype = DNA   length = 468
FEATURE                   Location/Qualifiers
misc_feature              1..468
                          note = IFNg precursor
source                    1..468
```

-continued

```
                              mol_type = other DNA
                              organism = synthetic construct
SEQUENCE: 4
gctcaatata catcaattaa tatgaaatca aatattgata aacttaaagt acattataaa    60
attagtaaag atcaattgtt taatggaaaa ccagtttttc ctaaagatac atttgaagat   120
tcagaacgta gagtttggat gtctgttgta ttagatgtat atcgttcaat ttttaatcaa   180
atgcttaatc aaacaggtga tcaagaagta cgtgaaagat tagatcaagt taaaggaaaa   240
gtacaagaaa ctcaaaaaca ttattttctt aaacgaattc cagaattgag aacacatttg   300
caaaatcttt gggctattga aactagtaat acaactgttc aaggaaaagc attgtcagaa   360
tttattacta tttatgaaaa agcttctaaa ttagcactta aaattcattt aaagaaagat   420
aatcgacgta aaagacgaca agcacaacga ttgaaaagta gtattatg                468

SEQ ID NO: 5             moltype = DNA   length = 25
FEATURE                  Location/Qualifiers
misc_feature             1..25
                         note = encoding an amino acid terminal sequence
source                   1..25
                         mol_type = other DNA
                         organism = synthetic construct
SEQUENCE: 5
ggaggtggga catcatcatc atcat                                          25

SEQ ID NO: 6             moltype = DNA   length = 20
FEATURE                  Location/Qualifiers
misc_feature             1..20
                         note = FW primer IFNg salmon
source                   1..20
                         mol_type = other DNA
                         organism = synthetic construct
SEQUENCE: 6
ccgtacaccg attgaggact                                                20

SEQ ID NO: 7             moltype = DNA   length = 21
FEATURE                  Location/Qualifiers
misc_feature             1..21
                         note = RV primer IFNg salmon
source                   1..21
                         mol_type = other DNA
                         organism = synthetic construct
SEQUENCE: 7
gccggcatta ctccatccta a                                              21

SEQ ID NO: 8             moltype = DNA   length = 20
FEATURE                  Location/Qualifiers
misc_feature             1..20
                         note = FW primer IL1b salmon
source                   1..20
                         mol_type = other DNA
                         organism = synthetic construct
SEQUENCE: 8
ccccattgag actaaagcca                                                20

SEQ ID NO: 9             moltype = DNA   length = 20
FEATURE                  Location/Qualifiers
misc_feature             1..20
                         note = RV primer IL1b salmon
source                   1..20
                         mol_type = other DNA
                         organism = synthetic construct
SEQUENCE: 9
gcaacctcct ctaggtgcag                                                20

SEQ ID NO: 10            moltype = DNA   length = 20
FEATURE                  Location/Qualifiers
misc_feature             1..20
                         note = FW primer TGF-B salmon
source                   1..20
                         mol_type = other DNA
                         organism = synthetic construct
SEQUENCE: 10
agctctcgga agaaacgaca                                                20

SEQ ID NO: 11            moltype = DNA   length = 20
FEATURE                  Location/Qualifiers
misc_feature             1..20
                         note = RV primer TGF-B salmon
source                   1..20
                         mol_type = other DNA
                         organism = synthetic construct
```

```
SEQUENCE: 11
agtagccagt gggttcatgg                                                20

SEQ ID NO: 12           moltype = DNA  length = 22
FEATURE                 Location/Qualifiers
misc_feature            1..22
                        note = FW primer gamma IP10 salmon
source                  1..22
                        mol_type = other DNA
                        organism = synthetic construct
SEQUENCE: 12
gtgtctgaat ccagaggctc ca                                             22

SEQ ID NO: 13           moltype = DNA  length = 22
FEATURE                 Location/Qualifiers
misc_feature            1..22
                        note = RV primer gamma IP10 salmon
source                  1..22
                        mol_type = other DNA
                        organism = synthetic construct
SEQUENCE: 13
tctcatggtg ctctctgttc ca                                             22

SEQ ID NO: 14           moltype = DNA  length = 23
FEATURE                 Location/Qualifiers
misc_feature            1..23
                        note = FW primer IFNg Lactis-IFNg
source                  1..23
                        mol_type = other DNA
                        organism = synthetic construct
SEQUENCE: 14
cacatttgca aaatctttgg gct                                            23

SEQ ID NO: 15           moltype = DNA  length = 21
FEATURE                 Location/Qualifiers
misc_feature            1..21
                        note = RV primer IFNg Lactis-IFNg
source                  1..21
                        mol_type = other DNA
                        organism = synthetic construct
SEQUENCE: 15
caatcgttgt gcttgtcgtc t                                              21

SEQ ID NO: 16           moltype = DNA  length = 21
FEATURE                 Location/Qualifiers
misc_feature            1..21
                        note = FW primer IL-6 salmon
source                  1..21
                        mol_type = other DNA
                        organism = synthetic construct
SEQUENCE: 16
ccttgcggaa ccaacagttt g                                              21

SEQ ID NO: 17           moltype = DNA  length = 22
FEATURE                 Location/Qualifiers
misc_feature            1..22
                        note = RV primer IL-6 salmon
source                  1..22
                        mol_type = other DNA
                        organism = synthetic construct
SEQUENCE: 17
cctcagcaac cttcatctgg tc                                             22

SEQ ID NO: 18           moltype = DNA  length = 23
FEATURE                 Location/Qualifiers
misc_feature            1..23
                        note = FW primer IL-12 salmon
source                  1..23
                        mol_type = other DNA
                        organism = synthetic construct
SEQUENCE: 18
tgacgctttt tctcaccggt tgt                                            23

SEQ ID NO: 19           moltype = DNA  length = 22
FEATURE                 Location/Qualifiers
misc_feature            1..22
                        note = RV primer IL-12 salmon
source                  1..22
                        mol_type = other DNA
```

```
                       organism = synthetic construct
SEQUENCE: 19
acgctttgca gcatgagctt ga                                              22

SEQ ID NO: 20          moltype = DNA   length = 20
FEATURE                Location/Qualifiers
misc_feature           1..20
                       note = FW primer eF1a salmon
source                 1..20
                       mol_type = other DNA
                       organism = synthetic construct
SEQUENCE: 20
gggtgagttt gaggctggta                                                 20

SEQ ID NO: 21          moltype = DNA   length = 20
FEATURE                Location/Qualifiers
misc_feature           1..20
                       note = RV primer eF1a salmon
source                 1..20
                       mol_type = other DNA
                       organism = synthetic construct
SEQUENCE: 21
ttctggatct cctcaaaccg                                                 20

SEQ ID NO: 22          moltype = DNA   length = 30
FEATURE                Location/Qualifiers
misc_feature           1..30
                       note = FW primer RpoS F. pyschrophilum
source                 1..30
                       mol_type = other DNA
                       organism = synthetic construct
SEQUENCE: 22
gaagatggag aaggtaattt agttgatatt                                      30

SEQ ID NO: 23          moltype = DNA   length = 30
FEATURE                Location/Qualifiers
misc_feature           1..30
                       note = RV primer RpoS F. pyschrophilum
source                 1..30
                       mol_type = other DNA
                       organism = synthetic construct
SEQUENCE: 23
caaataacat ctccttttc tacaacttga                                       30

SEQ ID NO: 24          moltype = DNA   length = 24
FEATURE                Location/Qualifiers
misc_feature           1..24
                       note = FW primer STAT1
source                 1..24
                       mol_type = other DNA
                       organism = synthetic construct
SEQUENCE: 24
gaccagcgaa cccaagaacc tgaa                                            24

SEQ ID NO: 25          moltype = DNA   length = 23
FEATURE                Location/Qualifiers
misc_feature           1..23
                       note = RV primer STAT1
source                 1..23
                       mol_type = other DNA
                       organism = synthetic construct
SEQUENCE: 25
cacaaagccc aggatgcaac cat                                             23

SEQ ID NO: 26          moltype = DNA   length = 19
FEATURE                Location/Qualifiers
misc_feature           1..19
                       note = FW primer rDNA 16S P. salmonis
source                 1..19
                       mol_type = other DNA
                       organism = synthetic construct
SEQUENCE: 26
agggagactg ccggtgata                                                  19
```

```
SEQ ID NO: 27           moltype = DNA  length = 19
FEATURE                 Location/Qualifiers
misc_feature            1..19
                        note = RV primer rDNA 16S P. salmonis
source                  1..19
                        mol_type = other DNA
                        organism = synthetic construct
SEQUENCE: 27
actacgaggc gctttctca                                                    19
```

The invention claimed is:

1. A method of preparing transformed *Lactococcus lactis* (*L. lactis*) bacteria to produce interferon gamma (IFNγ) comprising steps of:
   a) digesting a plasmid containing IFNγ with restriction enzymes NcoI and XbaI to form a digested product,
   b) purifying the digested product to form a first purified product;
   c) digesting a plasmid pNZ8149 with restriction enzymes NcoI and XbaI;
   d) purifying the plasmid pNZ8149 from an agarose gel to form a second purified product;
   e) ligating the first and second purified products from steps b) and d) with ligase to form a ligated plasmid;
   f) dialyzing the ligated plasmid; and
   g) transforming electrocompetent *L. lactis* bacteria NZ3900 with the ligated plasmid to form a transformed *L. lactis* bacteria having the accession number RGM 2416 comprising SEQ ID NO: 1, wherein SEQ ID NO: 1 is a DNA construct P1-USP45-IFNγ-GGG-6×His, wherein the DNA construct is within the plasmid pNZ8149, and wherein P1 is a *L. lactis* constitutive expression promoter;
Usp45 is a secretion signal;
IFNγ is the mature mRNA coding sequence for *Salmo salar* interferon gamma that is codon optimized for expression in *L. lactis*;
GGG is a sequence coding for three glycines; and
6×His is a sequence coding for 6 terminal histidines.

* * * * *